United States Patent
Wolf et al.

(10) Patent No.: US 11,915,151 B2
(45) Date of Patent: Feb. 27, 2024

(54) ACCURACY OF TEST DATA OUTSIDE THE CLINIC

(71) Applicant: Zoe Limited, London (GB)

(72) Inventors: Jonathan Thomas Wolf, London (GB); Richard James Davies, London (GB); George Hadjigeorgiou, London (GB)

(73) Assignee: Zoe Limited, London (GB)

( * ) Notice: Subject to any disclaimer, the term of this patent is extended or adjusted under 35 U.S.C. 154(b) by 1074 days.

(21) Appl. No.: 16/272,865

(22) Filed: Feb. 11, 2019

(65) Prior Publication Data

US 2020/0065681 A1  Feb. 27, 2020

Related U.S. Application Data

(60) Provisional application No. 62/723,429, filed on Aug. 27, 2018.

(51) Int. Cl.
*G06N 5/04*  (2023.01)
*G06N 20/00*  (2019.01)
*G16H 20/60*  (2018.01)
*G16H 10/40*  (2018.01)

(52) U.S. Cl.
CPC ............... *G06N 5/04* (2013.01); *G06N 20/00* (2019.01); *G16H 10/40* (2018.01); *G16H 20/60* (2018.01)

(58) Field of Classification Search
CPC .......... G06N 5/04; G06N 20/00; G16H 10/40; G16H 20/60; G16H 40/20
See application file for complete search history.

(56) References Cited

U.S. PATENT DOCUMENTS

| | | | |
|---|---|---|---|
| 7,999,674 B2 | 8/2011 | Kamen | |
| 8,690,578 B1 | 4/2014 | Nusbaum et al. | |
| 9,011,153 B2 | 4/2015 | Bennett et al. | |
| 11,250,950 B1 * | 2/2022 | Miller | G06F 18/214 |
| 2003/0091964 A1 | 5/2003 | Yeager | |
| 2009/0275002 A1 | 11/2009 | Hoggle | |

(Continued)

FOREIGN PATENT DOCUMENTS

| WO | WO0205702 | 1/2002 |
|---|---|---|
| WO | WO2008154759 A1 | 12/2008 |

(Continued)

OTHER PUBLICATIONS

Ewart R. Carson, Challenges for measurement science and measurement practice: the collection and interpretation of home-monitored blood glucose data, 1998, 13 pages (Year: 1998).*

(Continued)

*Primary Examiner* — Jennifer N Welch
*Assistant Examiner* — Parmanand D Patel
(74) *Attorney, Agent, or Firm* — Lee & Hayes, P.C.

(57) ABSTRACT

Techniques are disclosed herein for improving the accuracy of test data obtained outside of a clinical setting. Using the technologies described herein, different techniques can be utilized to analyze, score and adjust test data associated with one or more "at home" tests. In some examples, computing systems are utilized to generate quality scores indicating the accuracy of the test data associated with a particular biomarker. In other examples, an authorized user, such as a data manager can analyze the test data utilizing a user interface to generate scores and/or adjust the test data.

18 Claims, 8 Drawing Sheets

(56) References Cited

U.S. PATENT DOCUMENTS

| | | | |
|---|---|---|---|
| 2010/0083164 A1* | 4/2010 | Martin | G16H 40/63 715/835 |
| 2011/0053121 A1* | 3/2011 | Heaton | A61B 5/1495 600/365 |
| 2011/0091842 A1 | 4/2011 | Dugan | |
| 2013/0041343 A1* | 2/2013 | Toumazou | A61M 5/1723 604/504 |
| 2013/0216982 A1 | 8/2013 | Bennett et al. | |
| 2015/0079551 A1 | 3/2015 | Egan | |
| 2015/0093725 A1 | 4/2015 | Baarman et al. | |
| 2015/0118659 A1 | 4/2015 | Meyer | |
| 2015/0140523 A1 | 5/2015 | Dewan | |
| 2015/0206450 A1 | 7/2015 | Wayman et al. | |
| 2015/0294593 A1 | 10/2015 | Schoen et al. | |
| 2015/0294594 A1 | 10/2015 | Pacione et al. | |
| 2015/0371553 A1 | 12/2015 | Vento | |
| 2016/0035248 A1 | 2/2016 | Gibbs | |
| 2016/0042660 A1 | 2/2016 | Radovcic | |
| 2016/0049091 A1 | 2/2016 | Omidi | |
| 2016/0049092 A1 | 2/2016 | Barnett et al. | |
| 2016/0063888 A1 | 3/2016 | McCallum et al. | |
| 2016/0071423 A1 | 3/2016 | Sales et al. | |
| 2016/0071432 A1 | 3/2016 | Kurowski et al. | |
| 2016/0098942 A1 | 4/2016 | Messier | |
| 2016/0140869 A1 | 5/2016 | Kuwahara et al. | |
| 2016/0166195 A1 | 6/2016 | Radecka et al. | |
| 2016/0232311 A1 | 8/2016 | Segal et al. | |
| 2016/0253922 A1 | 9/2016 | Kremen et al. | |
| 2016/0379520 A1 | 12/2016 | Borel et al. | |
| 2017/0049386 A1* | 2/2017 | Abraham | G16H 20/17 |
| 2018/0018586 A1* | 1/2018 | Kobayashi | G06N 5/04 |
| 2018/0341898 A1* | 11/2018 | Bose | G06Q 30/0202 |
| 2019/0163666 A1* | 5/2019 | Cakmak | G06N 5/02 |
| 2019/0251861 A1 | 8/2019 | Wolf et al. | |
| 2019/0252058 A1 | 8/2019 | Wolf et al. | |
| 2019/0362648 A1 | 11/2019 | Hadjigeorgiou et al. | |
| 2019/0362848 A1 | 11/2019 | Wolf et al. | |
| 2020/0066181 A1 | 2/2020 | Hadjigeorgiou et al. | |

FOREIGN PATENT DOCUMENTS

| | | |
|---|---|---|
| WO | WO2015166489 | 11/2015 |
| WO | WO2018031991 | 2/2018 |

OTHER PUBLICATIONS

The PCT Search Report dated Sep. 3, 2019, for PCT Application No. PCT/EP2019/063330, 15 pages.

Non Final Office Action dated Jan. 10, 2020 for U.S. Appl. No. 15/894,776 "Generating Predicted Values of Biomarkers for Scoring Food" Wolf, 11 pages.

Non Final Office Action dated Jan. 10, 2020 for U.S. Appl. No. 15/894,798 "Generating Personalized Nutritional Recommendations Using Predicted Values of Biomarkers" Wolf, 12 pages.

Non Final Office Action dated Oct. 7, 2020 for U.S. Appl. No. 16/434,135, "Using at Home Measures to Predict Clinical State and Improving the Accuracy of at Home Measurements/Predictions Data Associated with Circadian Rhythm and Meal Timing", Wolf, 6 pages.

Non Final Office Action dated Dec. 10, 2020 for U.S. Appl. No. 15/987,699, "Improving the Accuracy of Measuring Nutritional Responses in a Non-Clinical Setting", Hadjigeorgiou, 12 pages.

The PCT Search Report dated May 21, 2019, for PCT Application No. PCT/IB2019/051088, 11 pages.

The PCT Search Report dated May 21, 2019, for PCT Application No. PCT/IB2019/051089, 12 pages.

Non Final Office Action dated Jul. 9, 2021 for U.S. Appl. No. 16/434,135, "Using at Home Measures to Predict Clinical State and Improving the Accuracy of at Home Measurements/Predictions Data Associated with Circadian Rhythm and Meal Timing", Wolf, 6 pages.

Office Action for U.S. Appl. No. 16/120,039, dated Mar. 22, 2021, Hadjigeorgiou, "Generating Personalized Food Recommendations from Different Food Sources", 12 pages.

The International Preliminary Report on Patentability dated Mar. 11, 2021 for PCT Application No. PCT/EP2019/072804, 9 pages.

Final Office Action dated Jul. 10, 2020 for U.S. Appl. No. 15/894,776, "Generating Predicted Values of Biomarkers for Scoring Food", Wolf, 6 pages.

Final Office Action dated Jul. 10, 2020 for U.S. Appl. No. 15/894,798, "Generating Personalized Nutritional Recommendations Using Predicted Values of Biomarkers", Wolf, 6 pages.

Anonymous, "Glucose meter—Wikipedia", retrieved on Oct. 30, 2019 at <<https://en.wikipedia.org/w/ index.php?title=Glucosemeter &oldid=851737873#Noninvasive_meters>>, Jul. 24, 2018, 15 pages.

Carson et al, "Challenges for measurement science and measurement practice: the collection and interpretation of home-monitored blood glucose data", Measurement, vol. 24, No. 4, Institute of Measurement and Control, Dec. 1, 1998, pp. 281-293.

Edelman et al, "Multisite Self-Test Evaluation of a New Diabetes Selt-Test for Glucose and Glycated Protein (Fructosamine)", Diabetis Technology & Therapeutics, vol. 2, No. 2, Jan. 1, 200, pp. 233-238.

Kulkarni, "Comparision of Image Recognition APIs on Food Images", retrieved on Oct. 19, 2019 at <<https://bytes.grubhub.com/https-medium-com-rohan-kulkarni comparison-of-image-recognition-apis-on-food-images-cddc9105fc33>>, pp. 1-9.

The PCT Search Report and Written Opinion dated Nov. 22, 2019 for PCT Application No. PCT/EP2019/072806, 15 pages.

The PCT Search Report and Written Opinion dated Nov. 8, 2019 for PCT Application No. PCT/EP2019/071801, 14 pages.

The PCT Search Report and Written Opinion dated Dec. 5, 2019 for PCT Application No. PCT/EP2019/072804, 14 pages.

Seeberg et al, "Development of a weable multisensor device enabling continuous monitoring of vital signs and activity", IEEE-EMBS International Conference on Biomedical and Health Informatics (BHI), IEEE, Jun. 1, 2014, pp. 213-218.

Tushuizen et al, "Postprandial lipid and apolipoprotein responses following three consecutive meals associate with liver fat content in type 2 diabetes and the metabolic syndrome", Atherosclerosis, vol. 211, No. 1, Elsevier, Amsterdam, NL, Feb. 10, 2010, pp. 308-314.

Von Niederhausern et al, "Validity of mobile electronic data capture in clinical studies: a pilot study in pediatric population", BMC Medical Research Methodology, vol. 17, No. 1, Dec. 1, 2017, 10 pages.

Wolcott et al, "Laboratory Medicine: A National Status Report Division of Laboratory Systems National Center for Preparedness, Detection, and Control of Infectious Diseases Centers for Disease Control and Prevention—The Lewin Group under Subcontract to Battelle Memorial Institute", retrieved on Nov. 25, 2019 at <<http://www.lewin.com/content/dam/Lewin/Resources/Site_Sections/Publications/39931>>, May 1, 2008, 385 pages.

Yun et al, "Smartphone-based point-of-care lipid blood test performance evaluation compared with a clinical diagnostic laboratory method", arxiv.org, Cornell University Library, Ithaca, NY, Apr. 19, 2018, 8 pages.

Office Action for U.S. Appl. No. 16/120,039, dated Sep. 14, 2022, Hadjigeorgiou, "Generating Personalized Food Recommendations from Different Food Sources", 10 pages.

Office Action for U.S. Appl. No. 16/120,039, dated Feb. 15, 2023, George Hadjigeorgiou, "Generating Personalized Food Recommendations from Different Food Sources", 10 pages.

* cited by examiner

ACCURACY OF TEST DATA OUTSIDE THE CLINIC

CROSS-REFERENCE TO RELATED APPLICATIONS

This application claims priority to U.S. Provisional Patent Application No. 62/723,429 entitled "Generating Personalized Nutritional Recommendations Using Predicted Values of Biomarkers," filed Aug. 27, 2018, which is incorporated herein by reference in its entirety.

BACKGROUND

Today, individuals can measure a large number of health characteristics without having to go to a lab or clinic. For instance, an individual may measure blood glucose, cholesterol, triglycerides, obtain biological samples (e.g., blood, biome), and the like from home or work, without having to visit a lab or clinic. These free living measurements are often cheaper, and can be easier for the individual to obtain as compared to going to a clinic. Free living measurements, however, can be less accurate than measurements taken in a clinical setting, such as in a hospital or a lab. For example, measurements obtained in a clinical setting are performed by clinicians that have been trained in the testing procedure, the testing instrumentation, and quality control practices. An individual performing a free living measurement, however, typically does not have this training. As a result, using these free living measurements performed by an individual to predict a health risk/health outcome can be less accurate.

DETAILED DESCRIPTION

Figure 1:
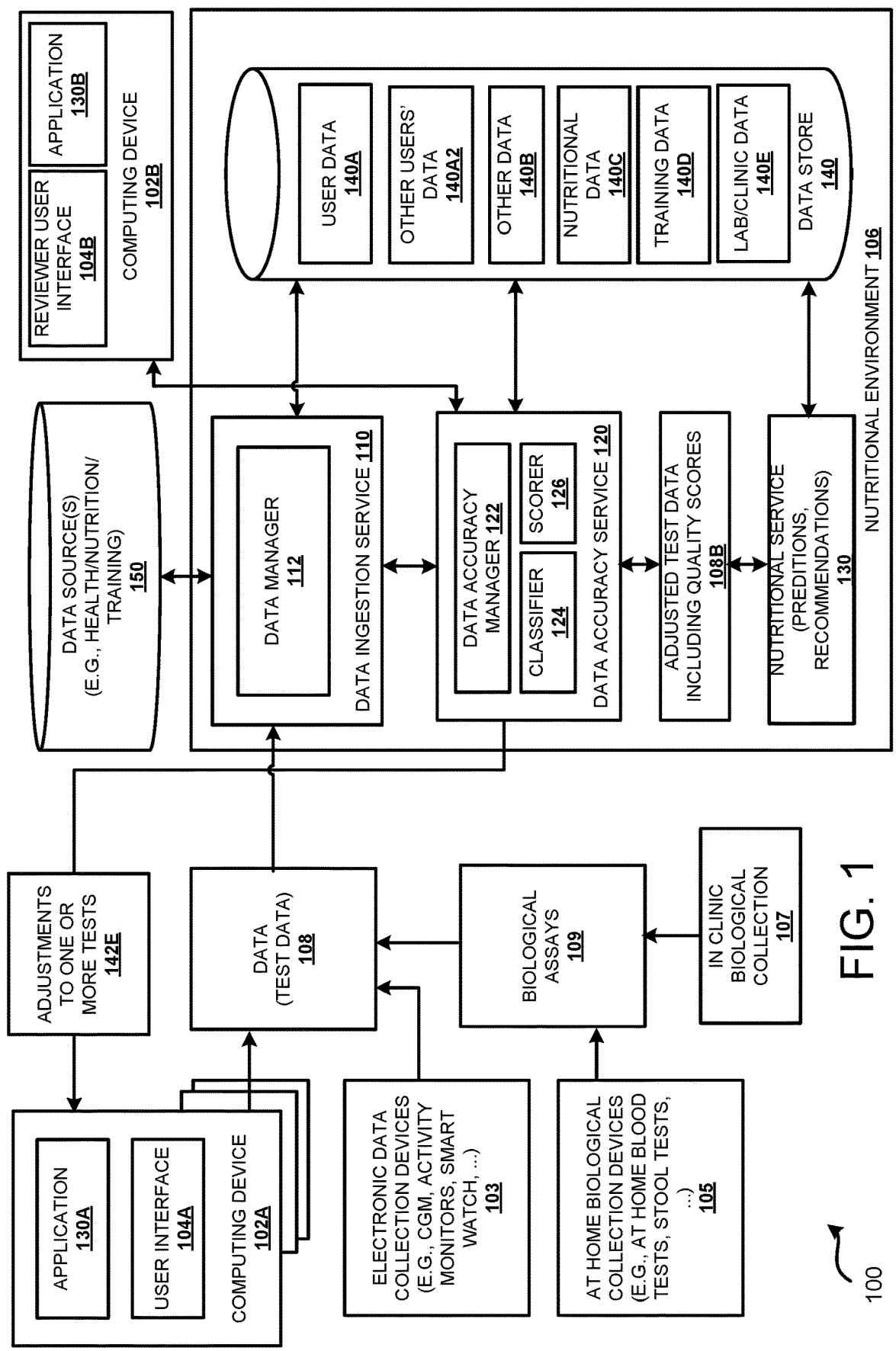
FIG. 1 is a block diagram depicting an illustrative operating environment in which test data associated with at home measurements of nutritional responses is analyzed to identify, score, and/or adjust inaccurate test data.

The following detailed description is directed to technologies for improving the accuracy of test data collected outside of a clinical setting. Using the technologies described herein, test data associated with the measurement and accuracy of nutritional responses recorded outside of a clinical setting are analyzed, scored, and/or adjusted to address detected inaccuracies. For example, test data associated with the measurement of nutritional responses for one or more biomarkers at home can be analyzed, provided with quality scores indicating a quality of the test data, and adjusted using the technologies described herein.

A "biomarker" or biological marker generally refers to a measurable indicator of some biological state or condition associated with an individual. Stated another way, a biomarker may be anything that can be used as an indicator of particular disease, state or some other physiological state of an organism. A biomarker can typically be measured accurately (either objectively and/or subjectively) and the measurement is reproducible (e.g., blood glucose, triglycerides, insulin, c-peptides, ketone body ratios, IL-6 inflammation markers, hunger, fullness, and the like).

The measured biomarkers can include many different types of health data such as microbiome data which may be referred to herein as "biome data", blood data, glucose data, lipid data, nutrition data, wearable data, genetic data, biometric data, questionnaire data, psychological data (e.g., hunger, sleep quality, mood, . . . ), objective health data (e.g., age, sex, height, weight, medical history, . . . ), as well as other types of data. Generally, "health data" can refer to any psychological, subjective and/or objective data that relates to and is associated with one or more individuals. The health data might be obtained through testing, self-reporting, and the like. Some biomarkers change in response to eating food, such as blood glucose, insulin, c-peptides and triglycerides and their lipoprotein components.

To understand the differences in nutritional responses for different users, dynamic changes in biomarkers caused by eating food such as a standardized meal ("post-prandial responses") may be measured. By understanding an individual's nutritional responses, in terms of blood biomarkers such as glucose, insulin and triglycerides levels, or non-blood biomarkers such as the microbiome, a nutritional service may be able to choose the food that is more suited for that particular person.

While clinical facilities are able to provide accurate post-prandial data, not only can the cost be prohibitive, the number of individuals agreeing to go to clinical facilities is limited. Bringing individuals into a clinical facility for multiple days to measure responses to different food is very expensive. If test data associated with at home measurements can be made sufficiently accurate, then much larger volumes of nutritional response data can be collected than has been possible historically.

Measuring post-prandial responses primarily outside of a clinical facility ("at home") can result in data that is not as accurate as desired. Clinical facilities typically generate accurate data and have therefore, historically, been utilized to obtain data associated with post-prandial responses. Generally, clinical facilities are able to generate accurate data amongst other reasons because (1) experiments are performed in controlled conditions to minimize contamination and maximize user compliance, (2) trained medical staff extract blood or collect other biological materials and use mechanisms such as a cannula to collect high quality samples of the material, (3) the biological samples can be treated to minimize inaccuracy by for example collecting in specially prepared tubes containing the right chemicals, centrifuging blood within the required time, and/or freezing samples at −80 degrees centigrade once extracted to prevent any changes to the sample, (4) sending the materials often still frozen to be measured with the highest quality assays.

At home tests, in contrast, do not appear to use these techniques. Using the techniques described herein, (1) the accuracy of the test data associated with at home tests can be improved over traditionally obtained at home measurements, and (2) by applying quality scores large amounts of data of differing accuracy and which may come from multiple people can be combined to maximize the accuracy and reliability of the recommendations generated.

The test data analyzed for inaccuracies can include a variety of data that is obtained from a variety of sources. For instance, test data can be obtained from questionnaires, camera, phone-based food logging, wearable devices (e.g., a Continuous Glucose Monitor), at-home biological collection devices (e.g. microbiome or blood collection), clinical labs, databases (e.g., nutritional databases), and the like.

To increase the accuracy of test data associated with measurements in a non-clinical setting, systems are utilized to analyze and rate the test data, to adjust the test data, and to apply quality scores to the test data. The systems can include computing devices (remote and/or local) and/or individuals authorized to analyze and adjust the test data. An individual authorized to analyze and adjust the test data may be referred to herein as an "analyst", or a "data analyst".

As an example, these systems can improve the accuracy of the test data by identifying errors or inaccuracies within the test data and then adjusting the test data to correct the inaccuracies. The systems may be configured to identify inaccuracies associated with food data, biome data, test data captured by a device, test data associated with a lab measurement, and the like. As an example, the systems may identify inaccurate food data, such as identifying errors in one or more of food classification, quantity of food estimates, timing data for meals, as well as other types of errors that may be introduced in a non-clinical setting. The systems can then adjust the data determined to be inaccurate (e.g., adjust a value or remove data) and/or apply a quality score (e.g. a measurement of the error in the data) such that other systems utilizing the data such as recommendation systems generate improved results.

According to some configurations, the systems may generate quality scores, or some other indication of accuracy, for the test data. These scores can be used to determine: whether to adjust the test data and how (e.g., change one or more values, remove inaccurate test data); how much should the test data impact a nutritional recommendation (e.g., inaccurate data having a lower quality score may be given less weight in a recommendation system compared to test data determined to be more accurate by a higher score); and/or how to adjust one or more parameters of a system, such as a nutritional recommendation system, that utilize the test data.

In some examples, the scores are generated by systems utilizing one or more machine learning mechanisms. In other examples, or as a way to provide training data to the computing systems using a machine learning mechanism or some other technique, a data analyst viewing the received test data may utilize different tools (electronic and/or non-electronic) to score/rate the test data. For example, as described in more detail below, one or more user interfaces may be utilized by the data analyst to score and adjust the test data.

As an example, a data accuracy service and/or a data analyst may receive and analyze data from one device and use data from a second device to identify its accuracy or adjust the result of the test. For instance, the test data obtained from a Continuous Glucose Meter (CGM) device may indicate a glucose spike even though there is not a corresponding entry of a logged food, a photo might not match a food description, food logging might not match self-reported eating habits from a questionnaire, the user may be logging too little food to cover their calorie requirements calculated from a questionnaire, data from a CGM may indicate a glucose spike too big for the food that was logged, and the like. These examples indicate issues with the data such that the data may be adjusted, rejected or have a lower quality score associated with it.

According to some configurations, one or more user interfaces ("UIs"), such as graphical user interfaces ("GUIs"), can be presented and utilized by a data analyst to view the test data and/or activity of users associated with the test data. The UIs may include user interface elements that are utilized by the data analyst to review the test data, compare the test data of the user with other test data, and the like. For example, a GUI can be displayed and presented to the data analyst that shows an image of a blood spot card associated with an at-home test. The data analyst can view the image within the GUI to determine if the blood spot was captured correctly (e.g., too much blood, too little blood).

The UI(s) can also provide one or more user interface elements to score the test data. Many different scoring mechanisms can be utilized (e.g., a value within a range of values, a classification such as good or bad, and the like). The UI(s) can also be utilized to adjust the test data. For example, one or more UI elements can be provided to allow the data analyst to adjust one or more values of the test data (e.g., correct a time, adjust a quantity of food, or remove an anomalous glucose spike), remove all or a portion of the test data associated with a particular test, and the like.

In some configurations, the UI, and/or some other system or component, can allow the data analyst or a system (e.g., a machine learning mechanism) to associate a quality score with the test data. This adjusted and quality scored data may then be provided to a recommendation system, or some other system for further use.

The UI can also be utilized to view photos that users have taken in addition to interacting with the other test data they have entered or provided (e.g., data associated with meals the user consumed). Upon reviewing the data, the data analyst may change data that a user has provided (e.g. to correct their recording of a particular food they ate, quantity they consumed, or timing of a meal or measurement.)

In some configurations, adjustments and/or ratings made by one or more data analysts can be stored and utilized as training data for one or more machine learning mechanisms. For example, the stored data can be utilized to generate a training data set by linking input test data with output data which might consist of corrected test data or quality scores applied to that test data. Examples of this includes evaluating photos of food to identify the food in the photo, identifying faulty CGM data or evaluating the quality of the food items recorded by a user associated with a photo.

In some cases, the UI, or some other component or system, can be used to update or provide nutritional information associated with the meals that the users have logged. This nutritional information can be imported from databases of food that have been created or imported from third parties. This can improve the computing mechanism's or support team's ability to identify whether food logging of a meal has been accurate by for example identifying that the quantities of macronutrients appear to be consistent with the food seen in a photo.

According to some examples, the system utilizes test data from many other users to improve the quality of the analysis and rating that it applies to that user's test data. As a result, the system may allow at-home measurements to be more accurate and useful than was historically possible.

According to some examples, a user may be provided a notification (e.g., an alert, a text message, an electronic mail, or some other indication) that indicates that at least a portion of the test data associated with an at home-measurement was identified as inaccurate. This notification may include information that assists the user in adjusting the at home measurements to obtain more accurate test data. In some configurations, the user may be provided notifications indicating an accuracy to the test data received over some period.

Additional details regarding the various components and processes described above relating to improving the accuracy of test data associated with tests measuring nutritional responses in a non-clinical setting will be presented below with regard to FIGS. 1-8.

It should be appreciated that the subject matter presented herein may be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures and other types of structures that perform particular tasks or implement particular abstract data types.

Those skilled in the art will also appreciate that aspects of the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, mobile telephone devices, tablet computing devices, special-purposed hardware devices, network appliances and the like.

In the following detailed description, references are made to the accompanying drawings that form a part hereof, and that show, by way of illustration, specific examples or examples. The drawings herein are not drawn to scale. Like numerals represent like elements throughout the several figures (which may be referred to herein as a "FIG." or "FIGS.").

FIG. 1 is a block diagram depicting an illustrative operating environment 100 in which test data associated with at home measurements of nutritional responses is analyzed to identify and adjust inaccurate test data and apply quality scores to the test data. An individual, such as an individual interested in obtaining personal nutritional recommendations, may communicate with the nutritional environment 106 using a computing device 102 and possibly other computing devices, such as electronic data collection devices 103.

In some configurations, one or more electronic data collection devices 103 can be used to collect some of the test data 108. For example, the electronic collection devices 103 could include a CGM, an activity monitor, a smart watch, and the like. These electronic data collection devices 103 may be worn on the body in which case they generate "wearable" test data. For instance, an individual may wear a fitness device, such as an activity-monitoring device, that monitors motion, heart rate, blood pressure and the like and can be used to determine how much an individual has slept, the number of calories burned, activities performed, body temperature, and the like. The individual may also wear a CGM that monitors blood glucose levels often by measuring levels of glucose in interstitial fluid. New devices are constantly becoming available to individuals. For example, devices for monitoring/measuring hydration status, metabolism, physical and psychological stress, sleep, and the like are becoming more readily available. Similarly, devices for measuring biomarkers are being developed for use by an individual. Generally, an electronic data collection device 103 can include existing devices as well as devices that have yet to be developed.

In some configurations, an individual may generate and provide test data 108 using a variety of at home biological collection devices 105, which collect a biological sample which requires a biological assay 109 to be performed to generate electronic test data 108. These devices may include but are not limited to "At Home Blood Tests" which use blood extraction devices such as finger pricks which in some examples are used with dried blood spot cards, button operated blood collection devices using small needles and vacuum to collect liquid capillary blood and the like. In some examples there may be home biological collection devices such as a stool test which is then assayed to produce biomarker test data such as gut microbiome data.

Some of the test data 108 may be biomarker test data, such as blood glucose results collected by the CGM. Some of this test data may be non-biomarker test data such as photos and time stamps.

An individual may also provide test data using computing device 102a. In some configurations an individual can input test data 108 into one or more software applications 130A. For example, an individual may enter the food they consumed, a value indicated by a measurement device, their waist measurement and the like.

In some examples, the user utilizes the computing device 102A to scan a barcode or QR code that is associated with food. The barcode can be used to correctly identify the food as well as the portion size of the food. In other configurations, some other identification technique, such as Near Field Communication (NFC), can be utilized to identify the food. As another example, an individual may input test data determined from one or more tests, such as urinalysis test strips, blood test strips, and the like. The test data may come from different sources, such as but not limited to from one or more of an individual, a lab, a doctor, an organization, and/or some other data source. In other instances, a camera of the computing device 102A can be used to capture photographic data such as digital photographs associated with a biological collection.

In other examples, the user may take one or more digital pictures of the food to generate test data that can identify the food. The image(s) can be programmatically analyzed to automatically identify the food within the image as well as the quantity of the food. The images might be taken before and after eating food such that a comparison can be made as to how much food was eaten. In addition to identifying the food, the computing device 102a can be used to identify other data about the event, such as the time of the event. This timing data, photographic data and other data may be considered non-biomarker test data.

The computing device might also be used to capture an image of a test performed by the user. For instance, the user can take a picture of a blood spot on a card. This image can then be programmatically analyzed (e.g., using a machine learning mechanism or some other procedure) or manually analyzed by one or more data analysts to determine that the captured blood spot meets one or more criteria (e.g., fills the spot, does not overfill the spot, . . . ). In other examples, an individual might scan a barcode or QR code of a test device, such as a blood spot card. The scan data can then be provided to the data ingestion service. The scan data may be used by the data accuracy service to correctly identify which test device was used for which test. This can be applied to other at home biological collection devices, including blood tests and stool tests and to confirm the order in which test meals are consumed.

Alternatively, and/or in addition to the above, data generated by other measurements can be used to assist in determining when a food was eaten, and/or a test was performed. For example, in some cases a CGM can be used to confirm the start point of a meal. In this example, data recorded by an individual about when they started to eat can be verified by confirming that there is a rise in glucose detected by the CGM, provided there was sufficient carbohydrate in the meal.

Instead of eating a single meal once and recording the nutritional response once, the test may be repeated one or more additional times to improve the accuracy of the at home testing, and identify the error associated with the measurement. The repeating of the eating of the same food can be used to obtain more accurate measurements of nutritional responses as compared to eating a single meal of the food.

According to some examples, two or more measurements of the same biomarker can be combined to increase the accuracy of the measurement of nutritional responses. In other examples measuring fasting bloods on more than one occasion and combining this data can be used to more accurately calculate baseline levels of biomarkers, and therefore improve calculations of nutritional responses.

A computing device, such as a mobile phone or a tablet computing device can also be used to improve the accuracy of the measurements. For instance, instead of relying on an individual to accurately record the time a test was taken, or a food was eaten, the computing device 102A can record information that is associated with the event. The computing device 102A may also be utilized to capture the timing data associated with the test (e.g., the time the food was consumed, the measurement(s) taken, . . . ) and provide that data to a data ingestion service. As an example, a clock (or some other timing device) of the computing device may be used to record the time the food was consumed and/or when the measurement(s) were collected.

According to some examples, at home meals/food consumed by the individual can consist of different nutritional compositions (e.g., carbohydrates/protein/fat . . . ). Varying the at home meals assists in obtaining a large range of nutritional responses. In some configurations, the individual is a customer of the nutritional environment 106 and the computing device 102A is a mobile computing device (e.g., a mobile phone).

As illustrated in FIG. 1, the operating environment 100 includes one or more computing devices 102, such as computing devices 102A and 102B in communication with a nutritional environment 106. In some examples, the nutritional environment 106 may be associated with and/or implemented by resources provided by a service provider network such as provided by a cloud computing company. The nutritional environment 106 includes a data ingestion service 110, a data accuracy service 120, a nutritional service 130, and a data store 140. The nutritional service 130 can be utilized to generate personalized nutritional recommendations. For example, the personalized nutritional recommendations can be generated using techniques described in U.S. patent application Ser. No. 15/894,798, filed on Feb. 12, 2018, which is incorporated by reference herein in its entirety.

The nutritional environment 106 may include a collection of computing resources (e.g., computing devices such as servers). The computing resources may include a number of computing, networking and storage devices in communication with one another. In some examples, the computing resources may correspond to physical computing devices and/or virtual computing devices implemented by one or more physical computing devices.

It should be appreciated that the nutritional environment 106 may be implemented using fewer or more components than are illustrated in FIG. 1. For example, all or a portion of the components illustrated in the nutritional environment 106 may be provided by a service provider network (not shown). In addition, the nutritional environment 106 could include various Web services and/or peer-to-peer network configurations. Thus, the depiction of the nutritional environment 106 in FIG. 1 should be taken as illustrative and not limiting to the present disclosure.

The data ingestion service 110 facilitates submission of data utilized by the data accuracy service 120 and, in some configurations, the nutritional service 130. Accordingly, utilizing a computing device 102, an electronic collection device 103, an at home biological collection device 105 or via in clinic biological collection 107, an individual may submit test data 108 to the nutritional environment 106 via the data ingestion service 110. Some of the test data 108 may be biomarker test data, and some of the test data 108 may be non-biomarker test data such as photos, barcode scans, timing data, and the like. Data may also be obtained by the data ingestion service 110 from other data sources, such as data source(s) 150. For example, the data source(s) 150 can include, but are not limited to nutritional data (e.g., nutrition of particular foods, nutrition associated with the individual, and the like), health data records associated with the individual and/or other individuals, and the like.

The data, such as data 108, or data obtained from one or more data sources 150, may then be processed by the data manager 112 and/or the data accuracy manager 122 and included in a memory, such as the data store 140. As illustrated, the data store 140 can be configured to store user data 140A, other users' data 140A2, other data 140B, and nutritional data 140C (See FIG. 2 for more details on the data ingestion service 110). In some examples, the user data 140A and other users' data 140A2 includes test data and health data that can include psychological data, subjective health data and objective health data. According to some examples, the test data 108 is associated with at home measurements of nutritional responses to food. In some examples, data sources 150 may include training data that can be obtained from a number of individuals (e.g., >100, 500, 1000, . . . ). This training data may be the results of at home and clinical measurements of nutritional responses using the same or different devices as used for the test data 108. This training data may include the results generated by using the data accuracy service 120 on the test data from these other individuals, such as adjusting certain test data. This training data can be provided to the data accuracy service 120 which may utilize a machine learning mechanism or other automated program to analyze the test data 108 associated with an at home measurement of a nutritional response, and adjust the test data or apply a quality score to it.

Some of the individuals in the training data may have been subject to similar tests and procedures as used to generate the test data. Some of the individuals in the training data may have generated data in a clinical setting using home collection devices at the same time as having high accuracy clinical measurements taken. This provides a high accuracy clinical measurement for a biomarker alongside the result generated by the at home measurement process. By providing the results of both these methods to the data accuracy service it is possible to adjust test data collected at home, so as to improve its accuracy. One example of this is measuring blood in clinic using venous blood collected by a trained practitioner and using the at home collection device such as a self-administered blood collection device collecting capillary blood at the same time.

As discussed in more detail below (See FIG. 3 for more details), the data accuracy service 120 utilizing the data accuracy manager 122 can analyze the accuracy of data 108 associated with an at home measurement of a nutritional response, and then adjust the values provided to a nutritional service, and associate a quality score with these values. As briefly discussed above, the at home measurements may be associated with at least two different at home sources of data (e.g., combining at home CGM and at home blood measurements, or combining time recorded on a computing device with blood measurements). The data accuracy service 120 can be configured to generate a score or a value indicating an accuracy of the test data, known as a quality score. In some examples, the data accuracy service 120 utilizes both data associated with the user providing the data and data from other users performing similar tests. In other examples, the data utilized is associated only with the user. According to some examples, the data can include test data obtained from a clinical setting, which is typically more accurate than at home measurements.

For instance, the data accuracy manager 122 may compare test data for fasting biomarkers measured at home with test data for fasting biomarkers measured in a clinical setting. According to some examples, it may use data to ascertain the accuracy of a particular data collection device and weight the data from that device accordingly compared to other devices. According to some examples, the data accuracy service 120 is configured to determine the level of accuracy of test data for the biomarkers associated with insulin, glucose, c-peptide, ketone bodies, triglycerides, IL-6 inflammation, microbiome, hunger, fullness, mood, and the like for an individual.

The data accuracy service 120 and/or a data analyst can also rate a user's overall compliance over a period of time such as a day, a week, etc. This data can be used to apply a quality score to all the data over this period. The UI 104B can be used to assist the data analyst and/or the data accuracy service 120 to make this decision by for example calculating the calories recorded by the user as being eaten during the whole day and comparing this with a calculation of the predicted basal metabolic rate adjusted for exercise of that individual based on the data they have provided (gender, weight, activity levels, etc.). The UI 104B may also provide one or more user interface elements to contact the user (e.g., via voice, email, chat, . . . ). The UI 104B can also be configured to provide reminders to a user to reschedule or repeat certain tasks (e.g. eating a particular meal or taking dried blood spots). In some examples, these reminders can be accessed by the application 130A such that the tasks are automatically performed.

In some examples, the data accuracy manager 122 may utilize one or more machine learning mechanisms. For example, the data accuracy manager 122 can use a classifier 124 to classify the accuracy of test data within a classification category. In other examples, the accuracy manager 122 may use a scorer 126 to generate a quality score that provides an indication of the likely level of accuracy of the test data for a biomarker. The results of analysts' ratings using the UI 104B can be used as part of the training data for this mechanism.

The data ingestion service 110 and/or the data accuracy service 120 can generate one or more user interfaces, such as a user interface 104A and/or user interface 104B, through which an individual, utilizing the computing device 102, or some other computing device, may provide/receive data from the nutritional environment 106. For example, the data ingestion service 110 may provide a user interface 104A that allows an individual of the computing device 102A to submit test data to the nutritional environment 106. The data accuracy service 120 may provide a user interface 104A that provides adjustments and/or instructions to the user for performing at home tests for nutritional responses.

As briefly mentioned above, instead of using a single at home test to measure one or more biomarkers (e.g., a blood glucose response) to a meal, the test may be repeated more than once to measure the one or more biomarkers. By combining the results from more than one test, the data accuracy service 120 can improve the level of accuracy of the calculated nutritional response. In some examples, the data accuracy service 120 determines accuracy of at home measurements for one or more of insulin, c-peptide, glucose, ketone bodies, hunger, energy levels, IL-6 inflammation and triglycerides. Insulin, glucose and triglycerides are metabolites that can affect body weight. The data accuracy service 120 can also be utilized with other at home measurements not specifically discussed.

In some cases, the individual can also provide biological samples to a lab for testing, using a biological collection device 105. According to some configuration this will include At Home Blood Tests. According to some configurations, individuals can provide a sample for microbiome analysis. As an example, metagenomic testing can be performed using the sample to allow the DNA of the microbes in the microbiome of an individual to be digitalized. Generally, a microbiome analysis includes determining the composition and function of a community of microbes in a particular location, such as within the gut of an individual. An individual's microbiome appears to have a strong relationship to metabolism, weight and health, yet only ten to thirty percent of the microbiome is estimated to be common across different individuals. Techniques described herein combine different techniques to assist in improving the accuracy of the data captured outside of a clinical setting, such as calculating accurate glucose responses to individual meals, which can then be linked to measures like the microbiome.

According to some configurations, individuals can provide a sample or samples of their stool for microbiome analysis as part of the at home biological collection, 105. In some cases, this sample may be collected without using a chemical buffer. The sample can then be used to culture live microbes, or for chemical analysis such as for metabolites or for genetic related analysis such as metagenomic or metatranscriptomic sequencing. In such cases it may suffer from changes in microbial composition due to causes including microbial blooming from oxygen in the period between being collected and when it is received in the lab, where it will be immediately assayed or frozen. In some cases, to avoid this change in bacterial composition after collection, the sample may be frozen at low temperatures very rapidly after collection. The sample can then be used to culture live bacteria, or for chemical analysis or for metagenomic sequencing. This collection can be done as part of an in clinic biological collection or at home where the collection kit is configured to deliver such low temperatures and maintain them until a courier has taken the sample to a lab.

A stool sample may be combined with a chemical preservation buffer such as ethanol as part of the at home collection process to stop further microbial activity, which allows a sample to be kept at room temperature before being received at the lab where the assay is done. This buffer allows for such a sample to be posted in the mail without issues of microbial blooming or other continuing changes in microbial composition. The buffer may however prevent some biochemical analyses from being done, and because preservation buffers are likely to kill a large fraction of the microbial population it is unlikely that samples conserved in preservation buffers can be used for cultivation assays.

In some cases, a user may do multiple stool tests over time, so that one can measure changes in the microbiome over time, or measure changes in the microbiome in response to meals, or changes in the microbiome in response to other clinical or lifestyle variations.

In some examples, the stool sample may be collected using a scoop or swab from a stool that is collected by the user using a stool collection kit that prevents the stool from falling into a toilet. Because there is a very high microbial load in the gut microbiome compared, for example, to the skin microbiome it is also possible that in some cases the stool sample is taken from paper that is used to clean the user's behind after they have passed a stool. This is only possible if the quantity of stool is large enough that the microbes from the stool greatly exceed the microbes that will be picked up from the user's skin or environmental contaminants. In any of these cases the scoop, swab or tissue may be placed inside a vial that contains a buffer solution. If the user then ensures the stool comes into contact with the buffer for example by shaking then this stops further microbial activity and allows the solution to be kept at room temperature without a significant change in microbial composition. In some cases, a sterile synthetic tissue can be used that does not have biological origins such as paper, so that when the DNA of the sample is extracted there is no contamination from the tissue. According to some examples, the tissue can be impregnated with a liquid to help capture more stool from the user's skin, where the liquid does not interfere with the results of the stool test and is not potentially dangerous for the human body.

In some cases, the timing and quality of the stool sample can be recorded using the computing device 102A, for example using a camera. Where there are multiple stool tests the computing device 120 can use a barcode (or some other identifier) to confirm the timing and identity of that particular sample. Other data can also be collected. For example, data about how the sample was stored, how long the sample was stored before being supplied to the lab for analysis, and the like.

While the data ingestion service 110, the data accuracy service 120, the nutrition service 130 are illustrated separately, all or a portion of these services may be located in other locations or together with other components. For example, the data ingestion service 110 may be located within the data accuracy service 120. Similarly, the accuracy manager 122 may be part of a different service, and the like.

At home measurements for different biomarkers can be obtained over some period of time. In some examples, the period individuals may perform at home measurements may range from one day to a few weeks. In other examples, the period ranges over some other duration. Generally, the longer the period the measurements are taken results in higher cost and more information gathered. There can also be a greater risk of non-compliance by the user as the duration of the measurements is lengthened. In other examples, there are multiple periods of measurement. For example, measurements may be taken at different points in time (e.g., every other day, once a week, every six months, over two weeks with a separate clinical visit a month later, . . . ). In some cases, the measurements are taken by electronic data collection devices 103, such as the Continuous Glucose Monitor (CGM), that have a limited operating duration. As discussed above, test data 108 can also come from other sources, such as at home biological collection devices 105, and/or in-clinic biological collection.

In order to assist in obtaining accurate measurements, the computing device 102, may be a mobile computing device (e.g., a mobile phone or tablet) that can be utilized to assist in improving the accuracy of the at home measurements of the nutritional responses. For example, an application 130 executing on the mobile phone, or at some other location, can be utilized to record different information associated with the at home measurements. The information captured by the computing device can include a variety of information, such as time of day, temperature, one or more pictures, textual input, voice input, barcode scans, QR code scans, and the like.

In some examples, the application 130 can be configured to operate without connectivity to the Internet. For example, the individual can take measurements and utilize the application to record information associated with the measurements, without Internet connectivity. When connectivity is restored, the application 130 can connect to the Internet to provide authorized information to one or more other computing devices. This can be helpful since people may eat out in locations with limited or no Internet access but would like to log their food as they are eating it. According to these configurations, the computing device may store at least the portion of a nutritional database that the user accesses to record food, in order to help ensure that data can still be captured by the application without Internet connectivity. In some examples, the information is provided to the one or more computing devices of the nutritional environment. The data accuracy service 120 can then analyze the information programmatically and/or manually and determine information and accuracy about the measurements being performed.

To provide a more complete understanding of determining nutritional responses to a particular food, an example protocol will now be described. It will be appreciated that changes can be made to the following steps and procedures.

In some examples, food item(s) selected for a particular test are standardized across different individuals. These "standardized meals" are carefully measured meals that can be packaged and eaten by the individual at home. Instructions are provided to the users to eat the meal at predefined times (e.g., after waking up without eating anything else.). In some examples, more than one meal is utilized. As will be discussed in more detail below, meals that include different nutritional ratios or composition may be included. The at home tests performed can include one or more blood tests that are taken at different points in time relative to when the meal is consumed, depending on biomarkers being measured.

If only a single meal is to be eaten, the components of carbohydrate, fat, protein ("macronutrients") and fiber are chosen to help ensure that on average there is a significant post-prandial change in the individual's target biomarkers. For example, if the target is to measure blood glucose and blood lipids, the meal will have significant carbohydrate levels (e.g. above 30 grams) and fat levels (e.g. above 20 grams.) If there are a series of standardized meals, the standardized meals can be chosen to expose the individual to a variety of meals so as to measure the interpersonal variability of biomarker responses. One example series of meal might explore a range of levels of macronutrients: (1) metabolic challenge (50 g fat, 85 g Carbohydrate); (2) high fat breakfast (35 g fat, 35 g Carbohydrate); (3) medium fat breakfast (22 g fat, 71 g carbohydrate), (4) low fat/high carbohydrate breakfast (9 g fat, 95 g Carbohydrate); (5) Oral Glucose Tolerance Test. (0 g fat, 75 g Carbohydrate). Other series of meals can be utilized. For example, another series of meals might explore different sorts of macronutrient composition such as varying type of carbohydrates with differing levels of processing (e.g. a bread using highly refined flour vs unrefined rye bread).

Not all meals provide the same amount of incremental information about a meal. For example, once the results of an Oral Glucose Tolerance Test ("OGTT") have been measured then the incremental information from a high carbohydrate breakfast made of processed carbohydrates may be small. The test series of meals may therefore be optimized to choose a set of meals that provide additional incremental information about personalized responses to food based on measuring the incremental information gained from different meals eaten by many individuals who have already had their responses measured. In some cases, the data accuracy service can choose a combination of standardized meals that is optimized for an individual that provides insight into the individual's responses within the limitation of a certain number of standardized meals.

In other examples, insulin post-prandial responses can be calculated by modelling insulin levels via c-peptide levels from at home blood measurements. C-peptide is released into the blood as a byproduct of the formation of insulin by the pancreas. A c-peptide test measures the amount of c-peptide in a blood or urine sample. Post-prandial c-peptide response can be used to provide an estimate of the insulin response. According to some examples, the accuracy of the at home measurements can be enhanced by lab/clinical measurements on the same user or other users using some combination of the same at home testing method and/or higher accuracy clinical assays.

Nutritional responses to these meals can be measured using one or more tests. In some examples, At Home Blood Tests can be utilized to not only identify the post-prandial response to these individual meals but may also be utilized to predict responses to meals that were not measured by for example building a model linking biomarker responses to the characteristics of the meal. This model can be implemented within a nutritional service 130 as described herein.

Some of these standardized meals can be designed to avoid some of the complexities of the food matrix, bioaccessibility and bioavailability. The complexities of the food matrix, bioaccessibility and bioavailability refer to fact that the amount of nutrients absorbed by the body are not the same as are measured in the lab for the food. As an example, the body extracts only about a third of the calories in whole almonds, but almost all of the calories in ground almonds. The standardized meals can also be designed to minimize the impact of non-nutritive bioactives which change the metabolism of the individual (e.g. polyphenols). Even simple products like wholemeal bread and cheese are in fact highly complex, leading to a risk of variability between apparently identical meals and a complex interplay of factors beyond the macronutrients in the meal. The standardized meals can be designed to try and keep factors other than the target nutrients constant (e.g. keeping levels of fiber and protein constant if only changes in fat and carbohydrate are to be measured). It is also possible to design a series of standardized meals to explore nutrients other than macronutrients (e.g. by changing the fiber in the meal but keeping the other components constant), or to compare a complex non-processed food (such as a bean, or rye bread) with the simplified foods described above.

One approach to providing standardized meals is to make muffins, using plain flour, baking powder, egg white, caster sugar, skimmed milk and oil. If the meals are muffins, many days' worth of food can be provided to the individual at one time as a muffin can be frozen and defrosted without significant changes to the food matrix and/or nutritional composition, unlike certain products such as cooked pasta.

The percentage of carbohydrate, fat and protein can be manipulated easily with such an approach while ensuring that the meal structure is the same. The oil utilized is standardized. There are multiple options including an oil that is representative of the average oil used in that country (for example with representative proportions of different SFA's such as myristic, palmitic, stearic as well as Unsaturated Fatty Acids (UFA) (UFAs's oleic, linoleic and alpha-linolenic) or a single oil such as high oleic sunflower oil ("HOS"). HOS, with around 80% oleic acid, is generally preferable as it elicits what could be described as an 100% lipaemic response. Other fats elicit variable lipaemic responses due to differences in solid fat content, TAG sn-2 positional composition and presence of medium chain fatty acids. Therefore, to distinguish difference between fats, HOS gives a clean 'reference response'.

In some examples, at least a portion of the standardized meals are consumed for the first meal of the day. Breakfast is chosen since over-night fasting provides a more stable baseline from which to measure changes due to a meal. Eating the standardized meal first helps to ensure that there is not an impact from food or meals eaten a few hours earlier prior to the standardized meal. In some cases, six or more hours is needed by some individuals to clear fat from their blood. As a result, blood measurement after some other meal, such as dinner may be affected by meals earlier in the day.

As discussed briefly above, the standardized meals may be repeated. Given the high degree of noise inherent in measuring nutritional responses at home, this increases accuracy by having multiple measurements of biomarker responses to the same meals which may be statistically combined to generate a more accurate measure of the individual's response to a particular meal. This may be done using the data accuracy service 120.

To further increase accuracy, meals may be labelled with a barcode (or some other identifier) as well as text such as "Day 1", "Day 2", etc. Prior to consuming the standardized meal, the individual scans the barcode with their computing device 102 which may be a mobile phone. In some examples, an application on the computing device presents a user interface that displays what standardized meal to consume. As an example, the user interface may display "Day 2 Meal". In some instances, the individual is not aware of the nutrients in the standardized meal to help minimize mistakes while ensuring the contents are blinded to the individual. Individuals may also receive notifications through their computing device as reminders. According to some examples, the order of the standardized meals is randomized. This allows adjustment for the impact of the order of previous meals on the reactions to the current one.

In some cases, individuals are allowed to have water, tea or coffee with their standardized meals. According to some examples, an individual can add skim milk, no sugar, and is instructed to make the coffee or tea using the same amount each morning and at the same time each morning when testing is performed. The individual can also be instructed to not consume more than one tea or coffee until the measurement period after the standardized meal is complete which might be three hours for example.

These standardized meals are designed so that most individuals can consume them all and have enough food that they will be willing to avoid eating anything more for the prescribed period of the measurements after eating. Individuals will be asked to consume the entire amount of food indicated for the standardized meals within a set period of time such as ten minutes and to record any left-over food.

As discussed above, the food data can be determined using different mechanisms. In some examples, food logging can be done via a computing device 102A, such as a mobile phone. Outside of the standardized meals in which nutritional responses are measured, individuals are free to eat and drink what they wish during a measurement period or can choose from a list of recommended foods provided to them. The individuals may be asked to track their meals, snacks and drinks on their mobile device. Individuals are also advised not to change their physical activity patterns during the course of the study. This helps to ensure more accurate results.

To improve data associated with a particular individual, individuals can be provided recommendations to increase the diversity of the food they eat, so as to measure the impact of a wider range of nutritional inputs (e.g. high fiber meals). For example, a recommendation can be provided by the nutritional service based on the foods logged by the application.

According to some examples, the individual logs the food items being eaten, the start time of the meal and the quantity consumed, and the like. This data may be analyzed by the data accuracy service 120 to identify any inaccuracies or errors associated with the food data. For example, does the photo confirm a log entry as to when a meal was consumed, and/or a quantity of food consumed.

In some examples, the user will provide data 108 that is not complete. For instance, the user may not know nutritional data for one or more foods and/or there is no nutritional information recorded about it in a database of foods ("unknown food") that the user accesses. In this example, the data accuracy service 120, or some other component or system, or data analyst utilizing UI 104B and computing device 102B can be used to identify that certain meals are missing nutritional information. According to some configurations, the data accuracy service 120 can request the user to perform some action as indicated by 142E. As an example, the user may be asked to take a photo of this food, take a photo of the food package nutritional labelling, or enter the food package nutritional labelling through the application 130A when recording the meal. The data 108 received by the data ingestion service 110 in response to the request can be utilized by the data accuracy service 120 and/or the data analyst at a later time.

The data analyst and/or the data accuracy manager 120 can then use the photos of the food and any other data 108 received or accessed to record the nutritional data of the food either through pictures of the packaging recording the foods nutritional data or by looking it up based upon the name of the food item. Where the food does not have nutritional information because for example it comes from a restaurant that was not in the database used by the computing device 102, this data may be located on the restaurant's web site or the data analyst, or some other user, may use their nutritional knowledge to map this to known foods in the database. As such, unknown foods can be replaced with correct nutritional information.

The system can also improve the overall quality of the data by applying a quality score to foods in the database of foods, by for example identifying data that is out of possible range for a nutrient, or where the source of the data is less trusted.

To increase the accuracy of the logging, the individual may use the phone's camera to take digital images of the food. In some examples, a photo of the food can be programmatically analyzed by the data accuracy service 120, or some other component, to determine the food(s) eaten (See FIG. 3). In some examples, individuals may place an object of a known size, such as a standardized card, with the food being eaten before taking a picture. In this way, the object provides a reference scale for the food being consumed. The purpose of this is to automate recognition of what the food is, and what the quantity is by referencing an object of known scale. To increase the accuracy of the logging, the individual identifies the food from an accurate food database of foods available in that country either by barcode scanning to identify the food or by text-based entry by the user. This database can be stored on the mobile phone and/or at some other location.

By combining user photos with a known item such as a card, with the accurate identity of the food logged by the user from a database and its quantity it is possible to build a large training set of photos of food with accurate labels. One can then utilize an algorithm to automatically estimate the correct food in the photo and its quantity. One can use the photo to automatically capture the start time of the meal, and to provide information to one or more data analysts to manually check the accuracy of the user's logging.

By using the computing device 102 to log standardized meals, the start time of consuming the standardized meals can be determined. When the standardized meals have a barcode that is scanned with the phone then it can be determined by the data accuracy service 120 that the correct standardized meal was eaten and that the meal was eaten at the right time. When it is determined that the correct meal was not eaten, the test data can be associated with the actual meal eaten.

According to some examples, some individuals may be asked to visit a clinic to combine at home data with data collected at a clinic. The purpose of the clinic visit is to allow much higher accuracy of measurement for a subset of the individual's data, which can then be combined with the lower-quality at home data. This can be used by the data accuracy service 120 to improve the quality of the at home data.

According to some examples, the day before the visit to the clinic, the individuals are asked to avoid taking part in any strenuous exercise and to limit the intake of alcohol. In some configurations, the data accuracy service 120 can analyze the data 108, such as data obtained from an activity tracker, to determine whether the individual followed the instructions of avoiding strenuous exercise. Similarly, the data accuracy service 120 may analyze the foods eaten by the individual by analyzing food data that indicates the foods eaten by the user. Individuals are provided with food instructions for the day before to avoid eating high fat or high fiber meals that may interfere with the results the following day. The individuals are asked to fast overnight and instructed to avoid eating or drinking anything except water from the night before their visit. The individuals will be encouraged to drink a lot of water as it will help with cannulation on the day of the visit. They will also be asked to avoid taking any self-prescribed medication on the day of their appointment but continue taking their doctor-prescribed medicines.

Individuals are instructed to arrive at the clinic in the morning. Following reception and fasting measurements (e.g. blood pressure or heart rate), the individuals are often cannulated. Blood is then taken regularly throughout the visit, so as to accurately capture post-prandial responses. If necessary blood can be centrifuged rapidly and stored in freezers on-site at −80 degrees centigrade, ensuring that clinical assays can be carried out with the highest accuracy of results. This means many metabolites can be measured that could not be measured at home, and that there will be a high degree of accuracy to the results.

At a certain time point when blood is being drawn via cannulation, the individuals will also undergo an "At Home Blood Test" at the clinic, just as if the test were performed at home. The results of this At Home Blood Test can then be correlated with the high-quality measurement done by biological assays on the venous blood, to improve the accuracy of other At Home Blood Test results, both for this individual and any other user of that at home biological collection device. In some configurations, the At Home Blood Test goes through a process as close as possible to the experience at home for example by mimicking the time and temperature conditions it would experience from collection through postal to delivery at the location where it is assayed. In some configurations, the data accuracy service 120 can compare results of one test with information collected during clinics about the accuracy of the at home biological collection device when determining an accuracy of the test data and use this information to adjust the test data 108B including quality scores that is then delivered to the nutritional service 130. For example, systematic biases may be able to be corrected, and error ranges computed. This can also be carried out for at home stool test devices, which may be compared with fresh samples immediately frozen and then assayed.

After a fasting blood draw, the individual consumes a standardized meal, which is consumed within a set time such as ten minutes to ensure consistency of start time across individuals. In the clinical visit this is likely to be a very high fat meal, to allow measurement of triglycerides responses as well as carbohydrates. In some cases, this first meal may be followed by a second meal roughly four hours after the first.

In some cases, this high fat meal may consist of two high fat muffins and a NESQUIK milkshake, or a similar drink. Nutrient profile: 869 kcal, 82 g carb, 55 g fat, 15 g protein, 2 g fiber. When there is a second meal it may consist of a muffin which might contain 600 kcal (75 g Carb, 25 g Fat). This is intended to (1) further differentiate triglycerides responses between individuals in the hours after this meal, and (2) elicit a second insulin & c-peptide response that can be measured during the clinical visit. It will also ensure individuals do not get hungry before the end of the clinical visit.

The clinical visit can also be used to allow trained staff to carry out anthropometric measures, such as waist and hip circumference, body weight and body fat composition, height, blood pressure (which can be done using an ambulatory blood pressure monitoring device) and heart-rate. This can be compared with at home measurements to identify the accuracy of measurements done by the individuals themselves. In some cases, the individuals can also have a scan such as a DEXA scan to measure further characteristics of the individual such as visceral fat. The nutritional environment can use data from this clinic visit to correlate data that can be measured at home with data like visceral fat that cannot, so as to predict measures of visceral fat and other measures that cannot be measured at home today.

The clinical visit can also be used to train individuals on aspects of the at home activities, such as food logging, completing At Home Blood Tests and using their electronic data collection devices, so as to improve compliance and accuracy. In some cases, the electronic data collection devices can be attached at the clinical visit to improve success rates.

There are multiple ways for an individual to carry out an At Home Blood Test to collect their own blood at home without needing a medical professional. Some of these include finger pricks onto dried blood spot cards or other absorbent materials so that the blood dries, finger pricks into collecting vessels so that the sample remains liquid, micro needles or micro filaments that in some cases may use vacuum to draw blood into collecting vessels so that the sample remains liquid, as well as other techniques developed or to be developed. Avoiding contamination or damage such as hemolysis to the blood sample during collection, accurate timing, conservation of the sample to avoid changes to its composition after collection and avoiding misattribution of samples are factors affecting the accuracy of a test. Because at home collection of bodily fluids introduces more noise and error into the measurement, techniques described herein can be utilized to reduce error. In order to improve the accuracy of these tests, more than one test can be combined. For instance, combining the At Home Blood Test results with other measurements such as blood glucose via a CGM may be utilized.

In a clinical visit, blood is taken at multiple occasions usually through a cannula to allow a graph of the post-prandial response of each biomarker to be produced, and the peak and area under curve calculated. This can mean blood is taken at up to ten different occasions. At home, it is not practical to take blood so many times, for cost reasons and due to compliance since blood-taking at home may involve some discomfort and may be time consuming. In some examples, to measure a post-prandial response at home, at least two blood tests are taken for a single meal. One blood test may occur just before the meal to measure the baseline for the biomarker, and one or more other measurements may be taken after eating the meal. Usually the meal will be at breakfast time, so the first measurement is a fasting measurement. Because only a few time points are taken, it is not possible to accurately plot the whole curve of the biomarker, and if no measurement is taken near the peak of the biomarker's value it is difficult to accurately estimate that peak. Therefore, to be able to use at home measurements of post-prandial responses, care must be taken to determine the optimal time points for the blood taking in order to have useful at home measurements of responses.

Post-prandial measurements are therefore timed to coincide with the peaks for the target biomarkers, or to measure the most relevant part of the response for understanding personalized responses. For example, measuring around one hour after eating a meal is optimized for peak c-peptide response, and around 4 hours after the meal is optimized for peak triglycerides response. In another example with triglycerides the most relevant measure may not be the peak value, but the level of triglycerides recorded beyond four hours when the lipoprotein components of the aggregate triglycerides that is measured will have remodeled leading to remnant triglyceride rich lipoproteins and an increased number of atherogenic lipoproteins. These times can be adjusted based on the particular biomarker being measured. In some examples, the timing of blood tests at home is determined based on measurement of the particular post-prandial response to that meal in a clinical setting to identify the average person's peaks for the target biomarker. In some examples an area under curve is desired to be modeled which uses at least two measures beyond the fasting measure.

If one wants to capture the post-prandial response of biomarkers which peak rapidly after meals (e.g. c-peptides), and those that peak slowly (e.g. fats such as triglycerides), then this, in some examples, uses at least three time points for blood collection on a single meal. For example, one before the meal (fasting), one measurement at around one hour after the meal, and another measurement at around four hours after the meal. This timing allows peak levels to be captured for a range of biomarkers and then compared between individuals.

The timing of tests performed at home affects how accurate are the results of the test, as many biomarkers change significantly and rapidly post-prandially. The clock used for recording the timing of the tests can be synchronized with the clock used by the CGM, and the clock used for the online food logging before the at home collection begins. This will allow the data to be accurately combined which may be done using the data accuracy service 120. If timing is inaccurate the values measured can be far from their true values. The application 130 operating on the computing device 102 can be programmed to adjust the clocks on the applications running on the device and/or data accuracy service 120 can determine the time differences between each of the clocks such that the data is correlated.

In some examples, to assist in determining these biomarker values, the computing device 102 (e.g., a mobile phone) can be utilized. The individual uses the computing device to record the timing of each At Home Blood Test, providing a timestamp to match to the eventual biological assay results, 109. This helps to identify if the tests are taken at the correct times. If the timing is off, the data accuracy service 120 may adjust the data, reject the data, or apply a quality score to the data so that it can be used with a lower level of weighting when combined with other test data.

In some examples, the computing device 102 (e.g. a mobile phone) provides a user interface 104 that automatically provides notifications to the individual of the correct timing of the At Home Blood Tests, to reduce the likelihood of forgetting to take them.

According to some configurations, the computing device 102A (e.g. a mobile phone) provides a user interface 104 that for each At Home Blood Test can be utilized to interact with an individual. For instance, the user interface 104A can be utilized to ask an individual to record a picture of the blood sample, to scan a barcode on the sample, to confirm the time of collection, and the like. This helps to ensure that (1) the sample has been taken and the timing of the sample is accurately recorded, (2) the quality of the sample is recorded/stored, (3) if the individual has used the wrong blood collection device (e.g. switched day 2 and day 3, or switched hour 1 and hour 4), this is identified and can be corrected by the data accuracy service 120.

Recording a photo of the samples and delivering it over the Internet, or some other medium, to a qualified support individual, such as a data analyst, can identify issues with the sample quality immediately. If the sample quality is not high, the data analyst can identify the issue causing this and speak to the user before the measurement period is finished and teach them how to improve their blood collection process rather than only discover this issue after the user has finished the process and the sample is measured by the biological assays 109. The data analyst can also provide a quality score for the sample. For instance, the data analyst can utilize the reviewer user interface 104B to provide the quality score for test data 108. As discussed herein, the data accuracy service 120 can also be used to programmatically determine the quality of the sample in combination with input from the data analyst or independent of the data analyst.

As discussed above, some of the At Home Blood Tests can involve finger pricks. These have not commonly been used for triglycerides. However, it is possible if clear instructions to avoid contamination are followed. Contamination can be a particular problem, as for example it is the concentration of glycerol in blood that is measured to determine triglyceride concentrations in most commercial assays, and glycerol is common in many hand creams, hair gels, etc. that end up on individual's fingers. To assist in resolving this, each individual is instructed to wash their hands very thoroughly with plenty of soap, then wash all the soap away with clean warm water for at least 30 seconds. Any traces of soap, hand cream, etc. contaminate the results so that they cannot be used. Alcohol wipes should not be used after cleaning the hand.

Blood from finger-pricks is commonly deposited onto paper called Dried Blood Spot cards where it dries. Dried blood spots (DBS) also rely on certain characteristics of the individual such as hematocrit. The error induced by different hematocrit levels and other characteristics that alter the area of dried blood that results from a given volume of liquid blood is one of the challenges in using DBS. By measuring DBS in the clinical setting for an individual, and comparing it with venous blood measured using traditional clinical biochemistry, using in clinic biological collection 107 and then biological assays 109, the impact of the individual's hematocrit and other individual characteristics can be calculated and subsequent measurements made in the at home setting can be adjusted for by the data accuracy service 120, increasing accuracy.

To capture relevant information that may affect nutritional responses, the individual can be asked to fill in questionnaires, via computing device 102A which might be a mobile phone. The data from these questionnaires can be used to increase the accuracy of at home measurement by automatically computing likely values for the individual, for example required calories per day which vary by body weight, or certain biomarker responses which may vary depending on sex. The data accuracy service 120 can then compare these with the values measured by devices and adjust resulting test data 108 accordingly.

According to some examples, as discussed briefly above, a Continuous Glucose Monitor (CGM) may be attached to the individual for some or all of the period they are being measured at home. This CGM may be attached by the individual themselves at home. The CGM's clock can be synchronized with the clock on the computing device 102A, usually by synchronizing both to Internet time.

By wearing a CGM it is possible to combine highly accurate glucose data with data captured by other devices. In particular this allows the measurement at home of both the glucose response and one or more other biomarkers to the same meal using an At Home Blood Test. This is beneficial since, for example, many meals that generate low glucose responses are low in carbohydrate but high in fat and it is therefore valuable to measure the fat responses in the blood in order to determine the likely health effects of such a meal rather than rely only on glucose results.

The CGM can also be used to check the timing and content of the meals. If a glucose spike is not triggered shortly after a meal that is known to lead to such spikes (for example most meals that have carbohydrates in them) then this can be used by the data accuracy service 120 to reinterpret the data from an At Home Blood Test, and either reject it or adjust for the correct starting point of the meal. The size of the spike can also help to identify the accuracy of the food logged, so for example if the glucose spike is higher than expected then this could suggest the quantity of food is more than was logged.

As briefly discussed, in some examples qualified individuals can be utilized to provide support to users. When a mobile phone is being used by the user, it is possible to allow such a data analyst to receive close to real-time information on the quality of the test data and how well the user is following any prescribed protocols. According to some configurations, the data analyst analyzes the data using reviewer user interface 104B. This information can be used: (1) To contact the user and improve their food logging, at home blood taking, or other measurement; (2) To quantify the quality of the test data coming from the user based on talking to the user (by phone, or via messages). So, for example, if the user says that they struggled to log a particular meal, the data from that meal could be removed while keeping other data; (3) To correctly log food that has not been accurately logged. Because a photo has been taken, the one or more data analysts can correct the logging of that food. This can be done by speaking to the user directly, or by identifying the food manually, or by building a machine learning algorithm to automatically identify the food. Where food has not been logged accurately, this can be cross-checked with one of the other measurements.

As insulin is not very stable once extracted, it is not a good candidate for at home measurements. To overcome this, c-peptide may be measured using At Home Blood Tests, and then the insulin level may be calculated from the value of the c-peptide. This works because c-peptide can be relatively stable over many days, especially if using dried blood tests or other blood collection methods which may be put in the fridge at home before sending them to be analyzed. To calculate insulin values from c-peptide, it is helpful to have a large benchmark of data from in clinic biological collections 107 comparing the calculated c-peptide levels using the At Home Blood Test process at the clinical visit with the known values of insulin measured very accurately using venous blood and clinical biochemistry at the same time as the At Home Blood Test process. Using this data set it is possible to take one or more c-peptide values from a user's At Home Blood Test(s) and calculate the insulin levels for that individual. This data would be further improved if that individual did a clinical visit to do in clinic biological collections 107 which would provide further data to calculate that individual's relationship between c-peptide and insulin. In some configurations, the data accuracy service 120 can utilize data received by many different users in determining whether or not a measurement is accurate. The data accuracy service 120 can utilize a data analyst, a machine learning, and/or some other mechanism to generate a quality score for the data.

The activity level of individuals can be monitored using electronic data collection devices 105 that include devices like accelerometers and heart rate measurement. These can be used to calculate exercise and sleep amongst other things. These can be used as another check by the data accuracy service 120, as for example it isn't possible to be running and doing blood tests at the same time, and it isn't a good baseline blood measurement if the individual has been awake for twelve hours or did not sleep the night before.

According to some examples, the sleep and wake times of individuals are measured at home. For instance, at home electronic data collection devices 103 can be used to accurately measure sleep and wake times for an individual. The sleep and wake times for an individual can then be used to improve the accuracy of predictions and to predict responses at certain times of day or given a certain amount of sleep. In some configurations, the data accuracy service 120 can utilize data (e.g., sleep data) received by many different users. The data accuracy service 120 can then utilize a data analyst, a machine learning, and/or some other mechanism to adjust this data 108B as well as providing the raw data to the nutritional service.

To improve the accuracy of at home measurements of nutritional responses, cross-checking can be performed by the data accuracy service 120, the support team including one or more data analysts, or some other computing device. For example, through cross-checking of various combinations of two or more of: questionnaires, photos taken by the mobile phone, food logged, CGM, At Home Blood Spot recording, activity level monitoring or other electronic data collection devices, and data recorded by the one or more data analysts a determination can be made as to whether the data is accurate. The cross-checking can be performed by the data analyst, and/or the data accuracy service.

Where there is a conflict between different inputs (e.g. the individual recorded one thing in the app but a wearable device says something different) as identified by the data accuracy service and/or a data analyst, the data point can be removed from consideration by the data accuracy service 120 or it can reduce its weighting in any machine learning algorithm or other analysis based upon this data.

This cross-checking can be used to determine whether an individual's food logging is missing, or the food is not accurately described. For example, this can be identified when there is a glucose spike measured by a CGM without the individual having logged food at that time, or where there is a photo that clearly does not match the food described via the food logging, or where the total calories logged for the day are too little to cover the calculated calorie requirements that come from questionnaire data. It can also be used to identify where an individual's accuracy of food timing is poor, for example where a CGM spike does not closely align with the timing they recorded for their At Home Blood Tests or their food logging. All or a portion of this can be taken into account by the data accuracy service 120.

According to some configurations, one or more user interfaces ("UIs"), such as graphical user interfaces ("GUIs"), can be presented and utilized by a data analyst to view the test data and/or activity of users. For example, a reviewer user interface 104B can be presented on a display associated with computing device 102B. The reviewer user interface 104B may include one or more UIs. The UIs can include user interface elements that are utilized by the data analyst to review the test data, compare the test data of the user with other test data, provide quality scores for the test data, and the like. For example, the reviewer user interface 104B can be displayed and presented to the data analyst that shows an image of a blood spot card associated with an at home test. The data analyst can view the image within the GUI to determine if the blood spot was captured correctly (e.g., too much blood, too little blood). In some examples, the data analyst may utilize 130B, data accuracy service 120 and/or some other device or component to identify, score, and adjust inaccurate data 108.

In some examples, the reviewer user interface 104B presents one or more user interface elements that are utilized by the data analyst to score the received data. As discussed above, the score provides an indication of the accuracy of the test data. Many different scoring mechanisms can be utilized (e.g., a value within a range of values, a classification such as good or bad, and the like). The UI 104B can also be utilized to adjust the test data. For example, one or more UI elements can be provided to allow the data analyst to adjust one or more values of the test data (e.g., remove a spike or other anomalous data), remove all or a portion of the test data associated with a particular test, associate a quality score with the test data, and the like.

In some configurations, the UI 104B, and/or some other system or component, can present one or more options to allow the data analyst to utilize one or other systems (e.g., executing a machine learning mechanism) to associate a quality score with test data. This adjusted data may then be provided to a recommendation system, a nutritional service 130, or some other system for further use.

According to some configurations, the data accuracy service 120 can be configured to provide notifications to a user, such as the user of computing device 102A. For example, a notification (e.g., an alert, a text message, an electronic mail, or some other indication) that indicates that at least a portion of the test data associated with an at home-measurement was determined to be inaccurate can be provided to a computing device associated with the user. This notification may include information that assists the user in adjusting the at home measurements to obtain more accurate test data. In some configurations, the user may be provided notifications indicating an accuracy to the test data received over some period. For example, a user may be recording nutritional responses in their non-clinical setting a single time, more than once in a few hours period, multiple times over a few weeks, and the like.

Figure 2:
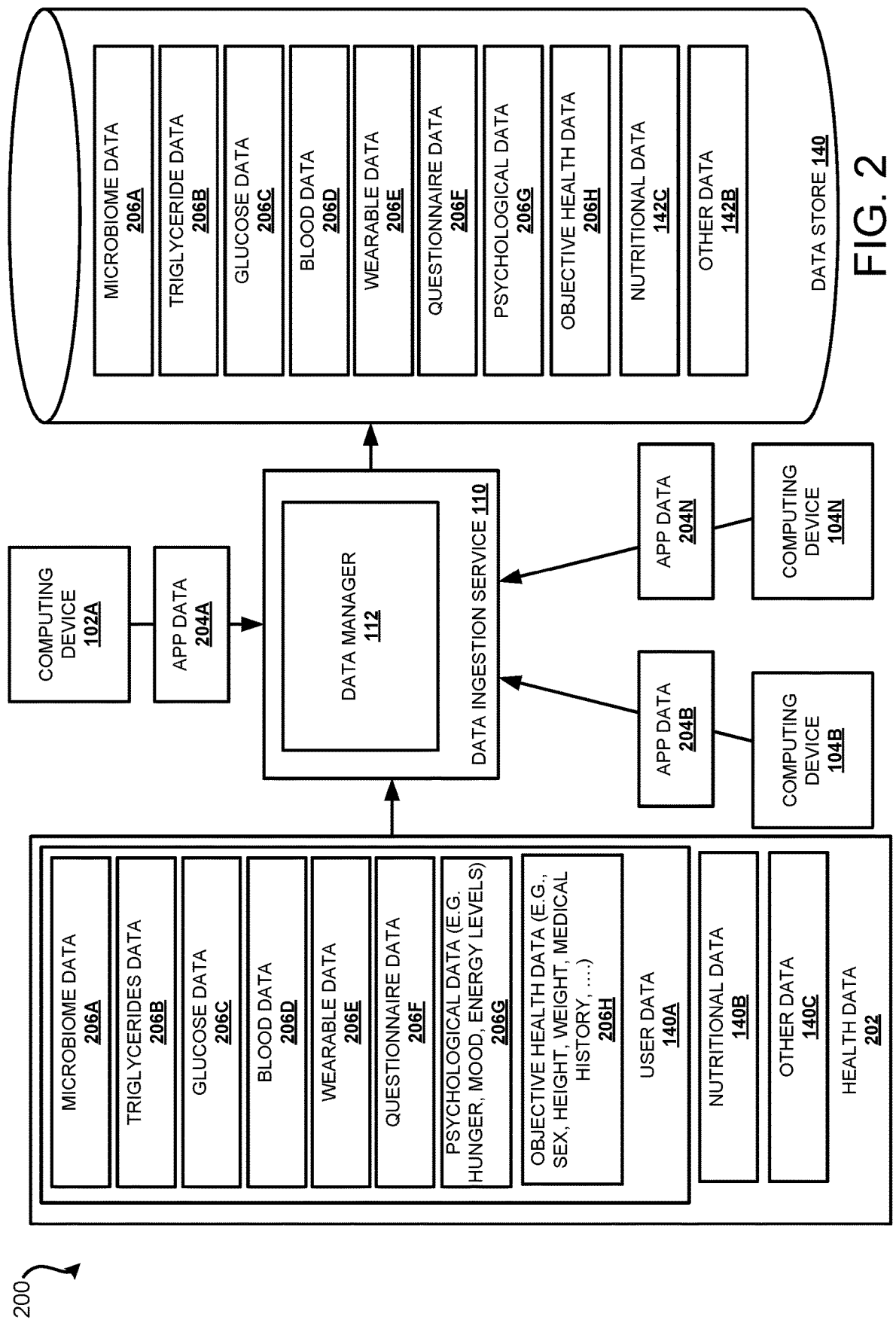
FIG. 2 is a block diagram depicting an illustrative operating environment in which a data ingestion service receives, and processes test data associated with at home measurements of nutritional responses.

FIG. 2 is a block diagram depicting an illustrative operating environment 200 in which a data ingestion service 110 receives and processes data associated with test data associated with at home measurements of nutritional responses. As illustrated in FIG. 2, the operating environment 200 includes the data ingestion service 110 that may be utilized in ingesting data utilized by the data accuracy service 120.

In some configurations, the data manager 112 is configured to receive data such as, health data 202 that can include, but is not limited to microbiome data 206A, triglycerides data 206B, glucose data 206C, blood data 206D, wearable data 206E, questionnaire data 206F, psychological data (e.g., hunger, sleep quality, mood, . . . ) 206G, objective health data (e.g., height, weight, medical history, . . . ) 206H, nutritional data 140B, and other data 140C.

According to some examples, the microbiome data 206A includes data about the gut microbiome of an individual. The gut microbiome can host a large number of microbial species (e.g., >1000) that together have millions of genes. Microbial species include bacteria, fungi, parasites, viruses, and archaea. Imbalance of the normal gut microbiome has been linked with gastrointestinal conditions such as inflammatory bowel disease (IBD) and irritable bowel syndrome (IBS), and wider systemic manifestations of disease such as obesity and type 2 diabetes. The microbes of the gut undertake a variety of metabolic functions and are able to produce a variety of vitamins, synthesize essential and nonessential amino acids, and provide other functions. Amongst other functions, the microbiome of an individual provides biochemical pathways for the metabolism of non-digestible carbohydrates; some oligosaccharides that escape digestion; unabsorbed sugars and alcohols from the diet; and host-derived mucins.

The triglycerides data 206B may include data about triglycerides for an individual. In some examples, the triglycerides data 206B can be determined from an At Home Blood Test which in some cases is a finger prick on to a dried blood spot card. The glucose data 206C includes data about blood glucose. The glucose data 206C may be determined from various testing mechanisms, including at home measurements, such as a continuous glucose meter.

The blood data 206D may include blood tests relating to a variety of different biomarkers. As discussed above, at least some blood tests can be performed at home. In some configurations, the blood data 206D is associated with measuring blood sugar, insulin, c-peptides, triglycerides, IL-6 inflammation, ketone bodies, nutrient levels, allergy sensitivities, iron levels, blood count levels, HbA1c, and the like.

The wearable data 206E can include any data received from a computing device associated with an individual. For instance, an individual may wear an electronic data collection device 103, such as an activity-monitoring device, that monitors motion, heart rate, determines how much an individual has slept, the number of calories burned, activities performed, blood pressure, body temperature, and the like. The individual may also wear a continuous glucose meter that monitors blood glucose levels.

The questionnaire data 206F can include data received from one or more questionnaires, and/or surveys received from one or more individuals. The psychological data 206G, that may be subjectively obtained, may include data received from the individual and/or a computing device that generates data or input based on a subjective determination (e.g., the individual states that they are still hungry after a meal, or a device estimates sleep quality based on the movement of the user at night perhaps combined with heart rate data). The objective health data 206H includes data that can be objectively measured, such as but not limited to height, weight, medical history, and the like.

The nutritional data 140B can include data about food, which is referred to herein as "food data". For example, the nutritional data can include nutritional information about different food(s) such as their macronutrients and micronutrients or the bioavailability of its nutrients under different conditions (raw vs cooked, or whole vs ground up). In some examples, the nutritional data 140B can include data about a particular food. For instance, before an individual consumes a particular meal, information about that food can be determined. As briefly discussed, the user might scan a barcode on the food item(s) being consumed and/or take one or more pictures of the food to determine the food, as well as the amount of food, being consumed.

The nutritional data can include food data that identifies foods consumed, a quantity of the foods consumed, food nutrition (e.g., obtained from a nutritional database), food state (e.g., cooked, reheated, frozen, etc.), food timing data (e.g., what time was the food consumed, how long did it take to consume, . . . ), and the like. The food state can be relevant for foods such as carbohydrates (e.g., pasta, bread, potatoes or rice), since carbohydrates may be altered by processes such as starch retrogradation. The food state can also be relevant for quantity estimation of the foods, since foods can change weight dramatically during cooking. In some instances, the user may also take a picture before and/or after consuming a meal to determine what food was consumed as well as how much of the food was consumed. The picture can also provide an indication as to the food state.

The other data 142B can include other data associated with the individual. For example, the other data 142B can include data that can be received directly from a computer application that logs information for an individual (e.g., food eaten, sleep, . . . ) and/or from the user via a user interface.

In some examples, different computing devices 102 associated with different users provide application data 204 to the data manager 112 for ingestion by the data ingestion service 110. As illustrated, computing device 102A provides app data 204A to the data manager 112, computing device 104B provides app data 204B to the data manager 112, and computing device 104N provides app data 204N to the data manager 112. There may be any number of computing devices utilized.

As discussed briefly above, the data manager 112 receives data from different data sources, processes the data when needed (e.g., cleans up the data for storage in a uniform manner), and stores the data within one or more data stores, such as the data store 140.

The data manager 112 can be configured to perform processing on the data before storing the data in the data store 140. For example, the data manager 112 may receive data for ketone bodies and then use that data to generate ketone body ratios. Similarly, the data manager 112 may process food eaten and generate meal calories, number of carbohydrates, fat to carbohydrate rations, how much fiber consumed during a time period, and the like. The data stored in the data store 140, or some other location, can be utilized by the data accuracy service 120 to determine an accuracy of at home measurements of nutritional responses performed by users. The data outputted by the data accuracy service 108B to the nutritional service may therefore contain different values than are stored in the data store 140, for example if a food quantity is adjusted.

Figure 3:
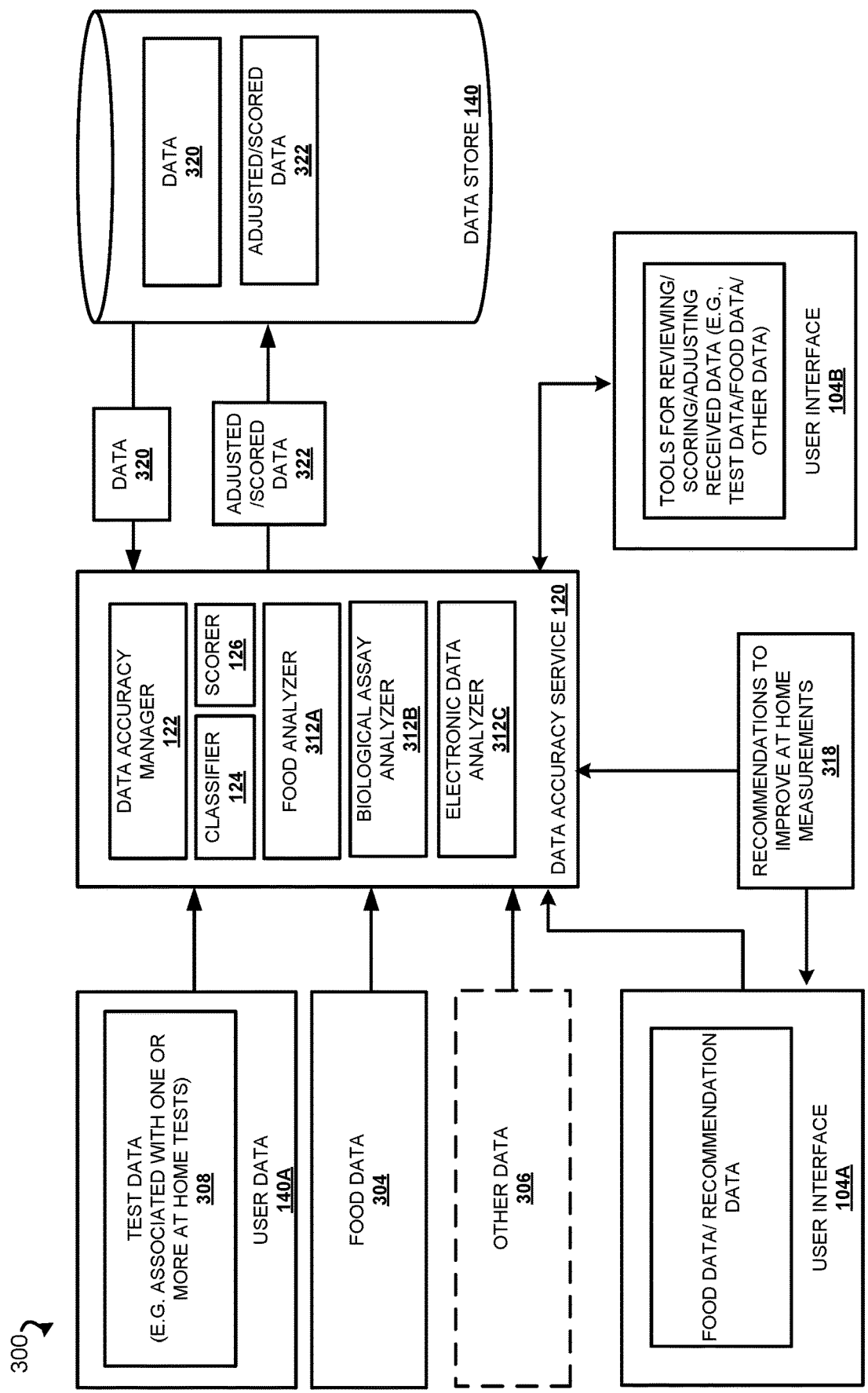
FIG. 3 is a block diagram depicting an illustrative operating environment in which a data accuracy service analyzes test data obtained in a non-clinical setting, generates one or more quality scores for the test data, and/or adjusts the test data and/or other parameters directed at improving the accuracy of the test data obtained in a non-clinical setting.

FIG. 3 is a block diagram depicting an illustrative operating environment 300 in which a data accuracy service 120 analyzes test data obtained in a non-clinical setting, generates one or more quality scores for the test data, and/or adjusts the test data and/or other parameters directed at improving the accuracy of the test data obtained in a non-clinical setting. As illustrated in FIG. 3, the operating environment 300 includes the data accuracy service 120 that includes data accuracy manager 122, classifier 124, scorer 126, food analyzer 312A, biological assay analyzer 312B and electronic data analyzer 312C.

As illustrated, the data accuracy service 120, via the data accuracy manager 122, receives user data 140A including test data 308, food data 304, and optionally other data 306. The accuracy manager 122 utilizes the user data 140A, the food data 304, and possibly other data 306 to analyze, score, and determine the accuracy of test data 308 associated with the at home measurement of one or more biomarkers. In some configurations, the data accuracy service 120 can utilize data 320 provided by data store 140 and/or some other data source. For instance, the data store 140 may include test data 320 that includes other users' data 140A2, other data 140B, nutritional data 140C, training data 140D, lab/clinic data 140E, and the like.

As illustrated, the data accuracy manager 122 is configured to analyze the data to identify any inaccuracies and/or errors associated with at home measurements of nutritional responses. As discussed above, biomarkers may be measured through one or more at home tests. The tests may include the use of a measuring device, and/or the collection of a bodily fluid (e.g., blood). For example, a portion of the test data 308 can be values of glucose levels, whereas another portion of the test data 308 can be values of insulin levels. As discussed herein, the test data 308 can include data associated with any at home test that measures a nutritional response and may include some data associated with in clinic collection which may include using at home measurements, devices, and/or traditional clinical measurement devices.

The food data 304 includes data that is associated with the food for which a nutritional response is being measured. The food data 304 can be input by the user either manually and/or automatically. For example, the user may select the food for a particular test from a menu or some other interface. In other examples, the user may scan a barcode of a food item(s) to identify the food associated with the test. In other instances, the user can capture one or more digital images of the food(s). As discussed above, the user may use a camera of a computing device to capture one or more images of the food(s) before the test and, in some examples, one or more images of any remaining food after the user has consumed the food(s). The food data 304 can include data that indicates foods consumed, a quantity of the foods consumed, food nutrition (e.g., obtained from a nutritional database), food state (e.g., cooked, reheated, frozen, etc.), food timing data (e.g., what time was the food consumed, how long did it take to consume, . . . ), and the like. The food state can be relevant for foods such as carbohydrates (e.g., pasta, bread, potatoes or rice), since carbohydrates may be altered by processes such as starch retrogradation. The food state can also be relevant for quantity estimation of the foods since foods can change weight dramatically during cooking. In some instances, the user may also take a picture after consuming a meal to determine what food was consumed as well as how much of the food was consumed. The picture can also provide an indication as to the food state.

According to some examples, the food analyzer 312A identifies the food(s) associated with the test(s) by analyzing the food data 304. As discussed above, the food analyzer 312A can identify food based on a barcode associated with the food, identify food that is identified within a captured image, or using some other technique or mechanism. For example, the food analyzer 312A may use object recognition to identify the food within an image as well as the quantity of food within the image. In some instances, the food analyzer 312A may request input from the user on identifying food that is associated with a test. The other data 306 might include data associated with an activity of the user, information about when the user last ate, and the like. The other data 306 might also include information from other users such as any at home and in clinic test results.

As discussed, the data accuracy service 120 can utilize a machine learning mechanism and/or receive input from a data analyst via a user interface 104B. The machine learning mechanism can be trained to identify whether test data associated with nutritional tests are accurate. The machine learning mechanism can also be utilized to generate a quality score for the test data. According to some examples, the machine learning mechanism, or some other scoring mechanism associates a quality score with the test data 308 according to its level of accuracy. For example, some test data 308 associated with a particular test for a biomarker may be more accurate than a different test for the same biomarker. Some data may be identified as inaccurate by the data accuracy manager 122 and/or the data analyst since value(s) are outside plausible biological ranges or because it is incompatible with other collected data. Further, the machine learning mechanism may use data received from individuals in a structured setting, such as a hospital setting, or a lab setting to assist in determining how accurate the data is, or to adjust the data for biases associated with the test.

According to some examples, the data accuracy manager 122 utilizes the scorer 126 to generate a quality score (e.g., a numerical value) for a particular test that measures a nutritional response for that user. In other examples, the accuracy manager 122 utilizes the classifier 124 to place the accuracy of the test data into a category (e.g., not accurate, average accuracy, high accuracy) or some other category (e.g., a category based on the value of the score). One factor that impacts the accuracy of a test that measures a nutritional response is how closely an individual follows the test protocol for the test being performed. For example, consuming the proper food (including the amount of food), performing the test at the appropriate time(s), and the like.

In some examples, the data accuracy service 120 determines whether data received from an individual performing a test is accurate. For instance, the data accuracy service 120 may determine that an individual incorrectly recorded the time the food was consumed and/or the time the test was taken based on the test data associated with the test (e.g., no glucose response detected after the user indicated a food was eaten that contained carbohydrates). In other examples, the data accuracy service 120 utilizing the biological assay analyzer 312B may detect whether the user correctly filled a bloodspot, and the like. For instance, the biological assay analyzer 312B can detect that not enough blood filled the bloodspot (e.g., by analyzing an image of a bloodspot to determine how much of the bloodspot is filled), that the bloodspot is filled correctly, or that the bloodspot is overfilled. The data accuracy service 120 can also use times recorded by a computing device to determine if the test was performed at the proper time. For instance, the time when an image is captured may be used to determine when the test was started. In other cases, the user might input the time when food was consumed and when the tests were performed. In other examples, the data accuracy service 120 utilizing the electronic data analyzer 312C may detect whether data from an electronic data collection device is accurate, for example if the output of an activity monitor falls within credible ranges for human activity. As discussed above, the data accuracy service 120 can utilize test data 308 as well as other data to determine whether the data match.

In some examples, the data accuracy service 120 utilizes data 320 obtained from the data store 140, or some other data source, when determining the accuracy of test data 308. For instance, the data accuracy service 120 may access test data obtained from clinical settings to determine an accuracy of test data received using an at home measurement. The data accuracy service 120 can also access other data associated with the user such as but not limited to questionnaire data 206F, psychological data 206G, objective health data 206H, and the like.

In some examples, increasing amounts of data are available in other data 306 as more and more participants participate in measurements outside a clinical study. This data can then be used by the data accuracy manager to improve its calculations of normal ranges for human activity, the accuracy of devices and the like.

In some configurations, a computing device 102, such as a mobile phone can be utilized to verify times when tests are performed, food is consumed, what food is consumed, and the like. These times can be used to assist in determining whether or not a test was performed within some predetermined amount of time from ingestion of the food (e.g., at 30 minutes, 1 hour, . . . ). As discussed above, other tests can be used to assist in determining an accuracy of a test. For example, values received from a CGM can be used to determine if the time associated with the ingestion of the food is consistent.

As discussed above, in addition to and/or alternatively, a data analyst can analyze the data to identify inaccurate data. For example, a data analyst may view one or more pictures/charts or other data to identify data that is inaccurate. As illustrated, the user interface 104B includes user interface elements that presents tools for analyzing, providing quality scores, and adjusting data associated with test data. In some examples this data can be used as training data for a machine learning algorithm employed by the data accuracy service 120.

The data accuracy service 120 can update data within the data store 140 based upon the analysis of the accuracy and adjustment of the test data 308. For example, the data accuracy service 120 may mark any test data that is determined to be inaccurate as not to be used. In some configurations, the data accuracy service 120 may mark test data as inaccurate based on the quality score associated with the test data. In some cases, the data accuracy service 120 can update the test data to a different value that is changed as a result of detecting inaccurate data. In yet other examples, the data accuracy service 120 can provide data that is used to weight some received test data lower compared to other test data. For example, test data that is classified as highly accurate may be given more weight compared to test data that is classified as acceptable.

The data accuracy service 120 can combine data to improve accuracy, for example by looking at multiple measurements of the same nutritional response. The data accuracy service 120 can correct for systematic error in a test result, for example where it calculates that a particular device such as an At Home Blood Test device consistently over-estimates or under-estimates the correct value for a particular biomarker.

The data accuracy service 120 can also provide recommendations 318 to the user to improve the at home measurements. For example, the data accuracy service 120 may provide the recommendations using user interface 104A. As briefly discussed above, the data accuracy service 120 can generate one or more user interfaces, such as a user interface 104A, through which an individual, utilizing the computing device 102, or some other computing device, may interact with the data accuracy service 120 and input or view data, such as the test data for nutritional responses or viewing the recommendations to improve the accuracy via the user interface 104.

FIGS. 4, 5, 6, and 7 are flow diagrams showing routines 400, 500, 600, and 700, respectively that illustrate aspects of improving the accuracy of test data associated with measuring nutritional responses in a non-clinical setting in accordance with examples described herein. It should be appreciated that at least some of the logical operations described herein with respect to FIGS. 4, 5, 6, and 7, and the other FIGS., may be implemented (1) as a sequence of computer implemented acts or program modules running on a computing system and/or (2) as interconnected machine logic circuits or circuit modules within the computing system.

The implementation of the various components described herein is a matter of choice dependent on the performance and other requirements of the computing system. Accordingly, the logical operations described herein are referred to variously as operations, structural devices, acts, or modules. These operations, structural devices, acts, and modules may be implemented in software, in firmware, in special purpose digital logic and any combination thereof. It should also be appreciated that more or fewer operations may be performed than shown in the FIGS. and described herein. These operations may also be performed in parallel, or in a different order than those described herein.

Figure 4:
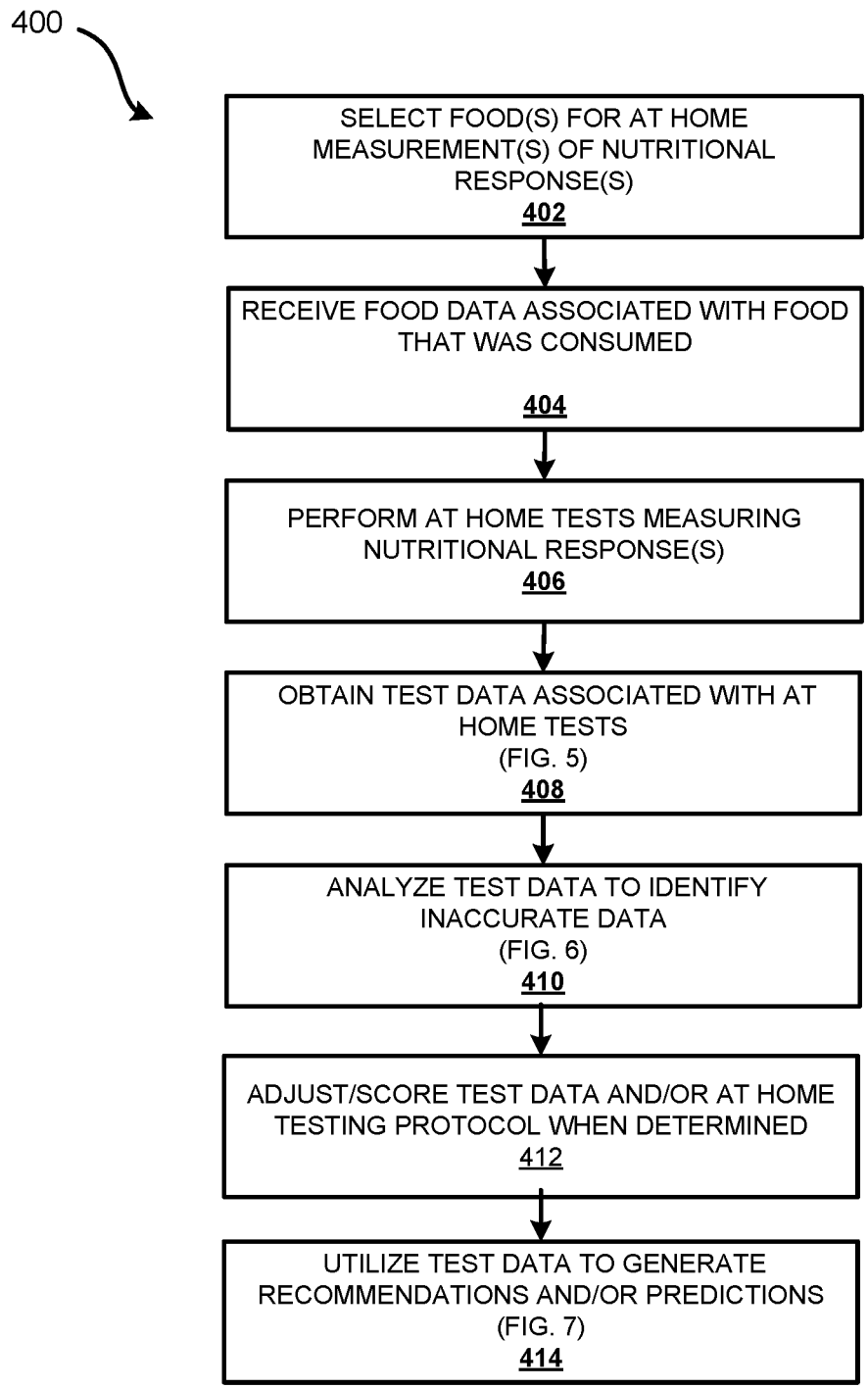
FIG. 4 is a flow diagram showing a routine illustrating aspects of a mechanism disclosed herein for improving the accuracy of test data obtained in a non-clinical setting.

FIG. 4 is a flow diagram showing routine 400 illustrating aspects of a mechanism disclosed herein for improving the accuracy of test data obtained in a non-clinical setting.

The routine 400 may begin at 402, where food is selected that is consumed to evoke a nutritional response. As discussed above, the food can be a series of standardized meals, a single meal, a single food, or some other selection of food.

At 404, food data is received. As discussed above, an individual may log the time the food was consumed. In other examples, the timing may be based on when an image was taken of the food to consume. In some configurations, the user can be instructed to take one or more pictures of the food before, during and/or after consuming the food. A user may also provide other data relating to the food, such as but not limited to the food state (e.g., cooked/raw, an age of the food, . . . ), how long it took to consume the food, and the like. According to some examples, a computing device 102A associated with the user provides the food data 304 to a data accuracy service 120 and/or a data ingestion service.

At 406, the at home tests measuring one or more nutritional responses are performed. As discussed above, the tests are performed at one or more points in time after eating a particular food, or foods of a meal. As also discussed above, the at home tests can include blood tests, and/or other tests that measure other biomarkers. In some examples, the individual may perform a blood test. In other examples, the individual may perform some other type of test. In some examples, tests are automatically carried out by electronic data collection devices. For instance, a measure of blood glucose can be taken, or the acceleration of a smart watch recorded.

At 408, the test data associated with the at home tests is obtained. As discussed above, the data ingestion service 110 can receive the test data from a computing device 102 or electronic data collection device 103 associated with the individual. In other examples, the test data is received from another source (e.g., the individual returns the collected biological sample via mail or some other courier service and a biological assay 109 is performed that outputs data to the data ingestion service 110). See FIG. 5 and related discussion for more details on receiving the test data.

At 410, the test data is analyzed by the data accuracy service 120 and/or one or more data analysts to identify inaccurate data. As discussed above, the data accuracy service 120 is configured to determine whether the test data collected by an individual is accurate. For example, was the test data obtained at a proper time as indicated by the test protocol for a particular test?, was the proper test data collected? (e.g., is the bloodspot filled correctly?), was the proper food consumed for the test?, was the proper amount of food consumed?, was the food properly classified?, and the like. As discussed above, the data accuracy service 120 can utilize data received from the computing device 102 (e.g., timing data, image data) to assist in determining whether the test protocol was followed. The data accuracy service 120 can also utilize one or more data analysts. See FIG. 6 and related discussion for more details on analyzing the test data to identify inaccuracies.

At 412, the test data and/or the at home testing protocol can be adjusted/scored when determined. As discussed above, the data accuracy service 120 may identify that a portion of the test data is inaccurate as a result of a testing protocol not being followed and provide instructions to the individual on steps to perform the test properly. The data accuracy service 120 can also adjust/remove the test data indicated to be inaccurate, as well as generate one or more quality scores for the test data.

At 414, the test data is utilized. In some examples, the test data is used by a nutritional service to generate nutritional recommendations that are personalized for a particular user. In other examples, the test data is used to calculate predicted health outcomes for a particular user. This test data may have been adjusted/scored by the data accuracy service 120. This test data may have been provided with a weight by the data accuracy service which is taken into account by the nutritional recommendation service, or some other service utilizing the test data (e.g., predict one or more health outcomes for an individual), which in some cases may involve machine learning mechanisms. See FIG. 7 and related discussion for more details.

Figure 5:
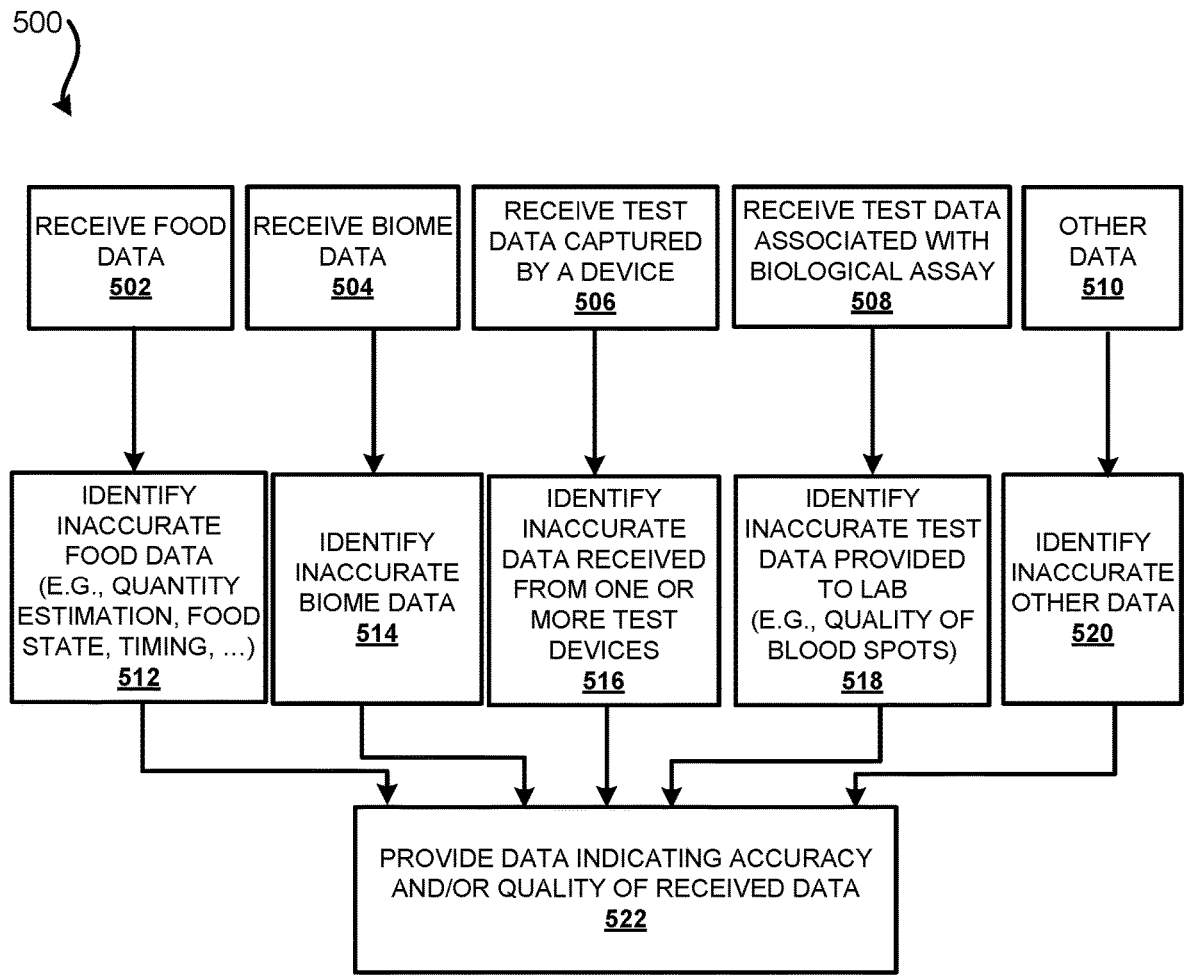
FIG. 5 is a flow diagram showing a routine illustrating aspects of a mechanism disclosed herein for obtaining test data associated with at home tests.

FIG. 5 is a flow diagram showing routine 500 illustrating aspects of a mechanism disclosed herein for obtaining test data associated with at home tests. The routine 500 may begin at 502, 504, 506, 508, and/or at 510 where data associated with tests performed in a non-clinical setting are obtained.

At 502, food data is received. As discussed above, the food data 304 is associated with foods that are utilized to evoke a nutritional response. The food data 304 can include foods for a series of standardized meals, a single food, or some other combination of foods. The food data 304 can include data such as foods consumed, a quantity of the foods consumed, food nutrition (e.g., obtained from a nutritional database), food state (e.g., cooked, reheated, frozen, etc.), food timing data (e.g., what time was the food consumed, how long did it take to consume, . . . ), and the like. The food state can be relevant for foods such as carbohydrates (e.g., pasta, bread, potatoes or rice), since carbohydrates may be altered by processes such as starch retrogradation. The food state can also be relevant for quantity estimation of the foods, since foods can change weight dramatically during cooking.

At 504, biome data is received. As discussed above, microbiome data 206A may be associated with one or more tests. In some configurations, the biome data includes a stool sample, timing data for the sample (e.g., when collected, how long stored before providing to a lab), data associated with collection of the sample (e.g., how was sample stored, was the sample contaminated), as well as other data. For example, a user may be instructed to take a picture of the sample and provide the image to the service.

At 506, test data captured by one or more electronic devices is received. For example, the test data may include wearable data 206E, as well as data captured/obtained from other sources. The electronic data collection devices 103 can include but are not limited to glucose monitors including CGMs, wearable activity trackers, blood pressure monitors, a QR code scanner, a digital camera, a computing device that provides timing data, collects data from one or more devices and/or the user, and the like.

At 508, test data associated with a biological assay is received. As discussed above, a user may perform a test at home that involves a biological sample being collected, provide to a lab e.g. by mail and then the lab analyzes this sample using a biological assay and provides the resulting test data. For instance, a user may be instructed to perform a finger prick, and then to fill a blood spot on a card with blood from the pricked finger. The test data associated with the lab measurement may include data such as timing data for the sample (e.g., when collected, how long stored before providing to a lab), data associated with collection of the sample (e.g., was the sample stored at room temperature, in a refrigerator, in a freezer, . . . ), one or more pictures of the sample (e.g., an image of the blood spot card), as well as other data.

At 510, other data associated with an at home measurement can be received. As discussed above, the other data can include data received from a user or some other source (e.g., questionnaire data 206F, psychological data 206G, objective health data 206H, nutritional data 140B, and the like).

Blocks 512, 514, 516, 518, and 520 are associated with analyzing the data to identify inaccurate data and to generate quality scores for the data. At 512, an accuracy of food data is identified. As discussed above, a data accuracy service 120 and/or a data analyst can analyze the received food data and generate a quality score (or some other indication) of the quality of the received food data. For example, all or a portion of the food data can be provided to a classifier/scorer 126 to generate the score(s) for the food data. In some configurations, the data accuracy service 120 utilizes one or more machine learning mechanisms to generate the score(s). In other configurations, all or a portion of the food data can be reviewed by a data analyst. For instance, a data analyst may utilize a GUI, such as user interface 104B, or some other interface to analyze the data and generate and/or provide the quality score(s).

According to some configurations, individual scores can be generated for the different types of food data received. For example, the quality scores can include a food classification score, a food estimation score, a food timing score, and the like that are determined by one or more of the data accuracy service and/or one or more data analysts. In some examples, the individual scores can be combined by the data accuracy service 120, or some other component or system, to generate an overall quality score for the test data.

At 514, inaccurate biome data is identified. As discussed above, a data accuracy service 120 and/or a data analyst can analyze the received biome data and generate a quality score (or some other indication) of the quality of the received biome test data. For example, all or a portion of the biome test data can be provided to a data accuracy service 120 and/or a data analyst to generate the score(s) for the biome test data. In some configurations, the data accuracy service 120 utilizes one or more machine learning mechanisms to generate the quality score(s) for the biome test data. In other configurations, all or a portion of the biome test data can be reviewed by a data analyst. For instance, a data analyst may utilize a GUI, such as user interface 104B, or some other interface to analyze the data and generate the quality score(s).

According to some configurations, individual quality scores can be generated for the different types of biome test data received. For example, a biome sample collection score, a biome test data timing score, and the like can be generated. In some examples, the individual quality scores can be combined by the data accuracy service 120, or some other component or system, to generate an overall quality score for the biome test data.

At 516, inaccurate test data obtained from one or more electronic data collection devices are identified. As discussed above, a data accuracy service 120 and/or a data analyst can analyze the received electronic device data and generate a quality score (or some other indication) of the quality of the received electronic device data. For example, all or a portion of the electronic device data can be provided to the data accuracy service 120 to generate the score(s). In some configurations, the data accuracy service 120 utilizes one or more machine learning mechanisms to generate the quality score(s) for the test data. In other configurations, all or a portion of the test data can be reviewed by a data analyst. For instance, a data analyst may utilize a GUI, such as user interface 104B, or some other interface to analyze the data and generate the quality score(s). In some examples, the system modifies data captured by a digital wearable device such as a continuous glucose monitor ("CGM") and/or applies a quality score to this data. For example, CGM data may be modified by applying filtering rules, such as excluding brief periods where readings are anomalously low or high, adjusting CGMs that have inaccuracies such as trending up or down over time, or adjusting the data to better estimate baseline glucose prior to a meal. In some cases, the data accuracy service 120 can evaluate CGM data by comparing timing of glucose rises compared to recorded meal times. In some cases, a data analyst may manually look at biomarker responses and generate a quality score that is used to determine whether this data should be shared with the user or used for a recommendation system.

The data accuracy service 120 may also apply quality scores to CGM data. For example, recording the quality of some or all of a particular CGM's readings as poor if the accuracy of the device is doubted. If a CGM is bumped or knocked while attached to a user or if the CGM becomes loose or gets wet, then this may impact the glucose reading recorded by the CGM. To help ensure inaccurate data is not used, the user can record this bump or other event e.g. via their smartphone app, and the system may choose to ignore a certain period of time of readings. This approach can also be used to ignore initial readings when a CGM is not yet accurately calibrated (e.g. the first 12 or 24 hours for a particular device). A same or similar approach can be taken to digital devices such as smart watches or accelerometers. Data can be filtered to remove spurious data, such as when the device was not worn.

According to some configurations, individual quality scores can be generated for the different types of electronic device data received. For example, an electronic device collection score, an electronic device data timing score, and the like can be generated. In some examples, the individual scores can be combined to generate an overall score for the electronic device data.

At 518, inaccurate test data associated with a biological assay is identified. As discussed above, a data accuracy service 120 and/or a data analyst can analyze the received test data associated with a biological assay and generate a quality score (or some other indication) of the quality of the received test data. For example, all or a portion of the test data can be provided to a computing system to generate the score(s) for the test data. In some configurations, the data accuracy service 120 utilizes one or more machine learning mechanisms to generate the quality score(s) for the test data. In other configurations, all or a portion of the test data can be reviewed by a data analyst. For instance, a data analyst may utilize a GUI, such as user interface 104B, or some other interface to analyze the data and generate the quality score(s).

According to some configurations, individual quality scores can be generated for the different types of test data received. For example, a sample collection score, a test data timing score, and the like can be generated. In some examples, the individual quality scores can be combined by the data accuracy service 120, or some other component or system, to generate an overall quality score for the test data.

At 520, inaccurate other data is identified. As discussed above, a data accuracy service 120 and/or a data analyst can analyze the received other data and generate a quality score (or some other indication) of the quality of the received other test data. For example, all or a portion of the other test data can be provided to a data accuracy service 120 and/or data analyst to generate the quality score(s) for the other test data. In some configurations, the data accuracy service 120 utilizes one or more machine learning mechanisms to generate the quality score(s) for the other test data. In other configurations, all or a portion of the other test data can be reviewed by a data analyst. For instance, the data analyst may utilize a GUI, or some other interface to analyze the other test data and generate the quality score(s). According to some configurations, individual scores can be generated for the different types of other test data received.

At 522, data indicating the accuracy, and/or the quality is provided. As discussed above, the data can be provided to one or more other systems to adjust the test data, adjust one or more systems utilizing the test data, and/or utilize the test data.

Figure 6:
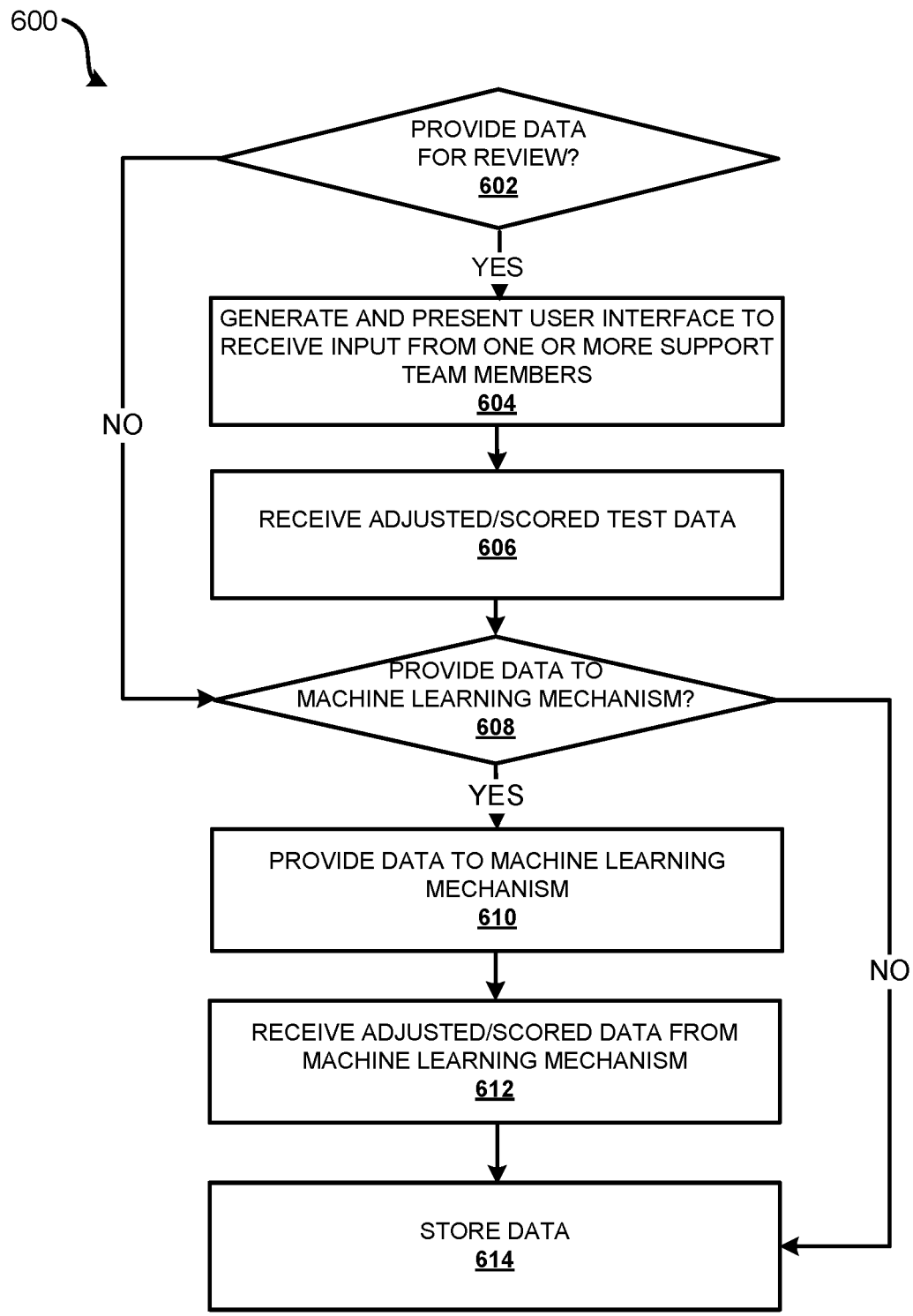
FIG. 6 is a flow diagram showing a routine illustrating aspects of a mechanism disclosed herein for scoring and analyzing test data to detect inaccuracies.

FIG. 6 is a flow diagram showing routine 600 illustrating aspects of a mechanism disclosed herein for analyzing test data to detect inaccuracies and to generate one or more quality scores for the data.

The routine 600 may begin at 602, where a determination is made as to whether to provide data for review by one or more data analysts. As discussed above, none, a portion, or all of the test data can be provided to one or more data analysts for review and/or scoring. The decision can be based on the type of test data received, an availability of data analysts, previous test data received from a particular individual, an importance of the test data, and the like. When the test data is to be reviewed by a data analyst, the process 600 moves to 604. When the test data is not to be reviewed by a data analyst, the process 600 moves to 608.

At 604, a user interface is generated and presented to one or more data analysts. As discussed above, the UI may be a GUI 104B that provides UI elements for reviewing, analyzing, scoring and adjusting test data and/or submitting at least a portion of data to a machine learning mechanism for analysis.

At 606, the adjusted test data is received. As discussed above, none, a portion, or all of the test data can be adjusted by one or more data analysts. Generally, the adjusted test data is the test data adjusted to remove inaccuracies. For example, inaccurate data can be removed from the test data, one or more values of the test data can be adjusted, and the like.

At 608, a determination is made as to whether to provide the data to a machine learning mechanism. As discussed above, one or more machine learning mechanisms, or some other system or technique, can be utilized to analyze, score, and adjust the test data. When test data is provided to a machine learning mechanism, the process 600 moves to 610. When test data is not to be provided to a machine learning mechanism, the process 600 moves to 614.

At 610, all or a portion of the test data is provided to a machine learning mechanism. As discussed above, the test data can be provided to a data accuracy service 120 and/or the test data can be accessed by the machine learning mechanism from a memory and/or some other data store.

At 612, data is received from the machine learning mechanism. As discussed above, the machine learning mechanisms can provide scoring data for the test data, adjusted test data and/or parameters to adjust one or more other systems.

At 614, the adjusted data is stored. As discussed above, the adjusted data can be stored for later use by one or more other systems. For example, a recommendation system can utilize the adjusted data to provide nutritional recommendations.

Figure 7:
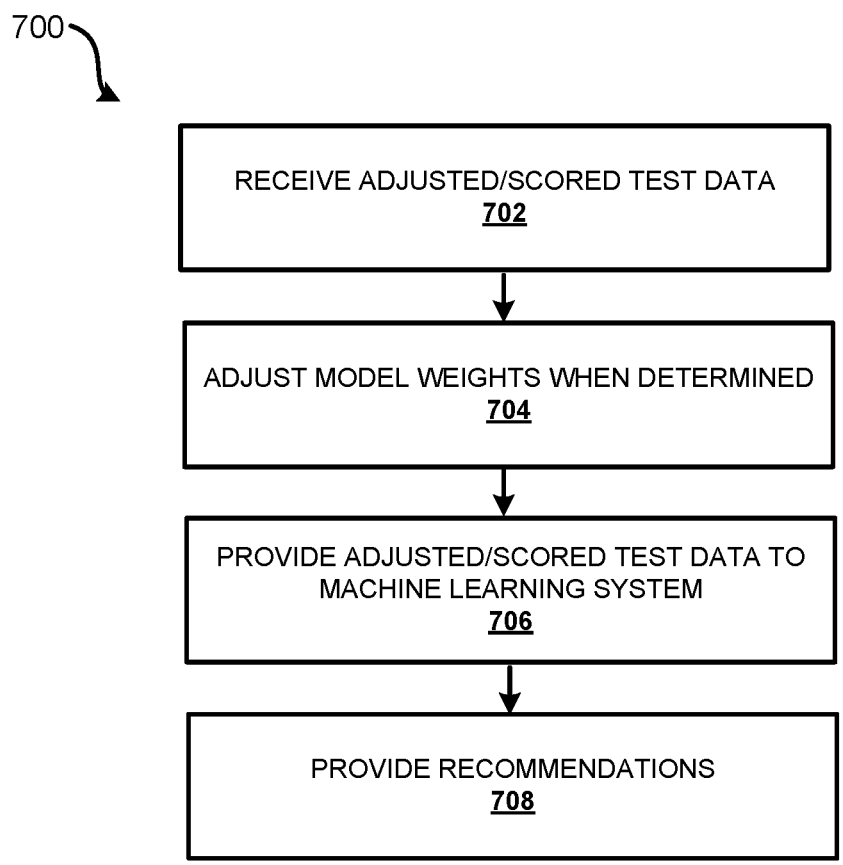
FIG. 7 is a flow diagram showing a routine illustrating aspects of a mechanism disclosed herein for utilizing test data scored and/or adjusted for inaccuracies to generate predictions and/or recommendations.

FIG. 7 is a flow diagram showing routine 700 illustrating aspects of a mechanism disclosed herein for utilizing test data scored and/or adjusted for inaccuracies to generate predictions and/or recommendations.

The routine 700 may begin at 702, where the adjusted/scored test data is received. As discussed above, the adjusted/scored test data can be received from one or more different systems. For example, the adjusted/scored test data can be generated by a data accuracy service 120 and/or generated by a data accuracy manager 122, one or more data analysts, and the like.

At 704, one or more model weights are adjusted when determined. As discussed above, instead of or in addition to adjusting the test data, one or more model weights can be adjusted to take into account the inaccurate test data. Adjusting the model weights can affect how much weight is placed on particular data when utilizing the data.

At 706, the adjusted/scored test data is provided to a machine learning system. As discussed above, the machine learning system can be utilized to generate predictions of health outcomes for a user, nutritional recommendations for a user, update/generate scores for the test data, and the like. Generally, the adjusted/scored test data can be utilized for many different purposes.

At 708, the predictions and/or recommendations are provided to a user. As discussed above, the recommendations can be nutritional recommendations that indicate what foods a user is to consume. In other examples, the predictions can be health outcome predictions for a user.

Figure 8:
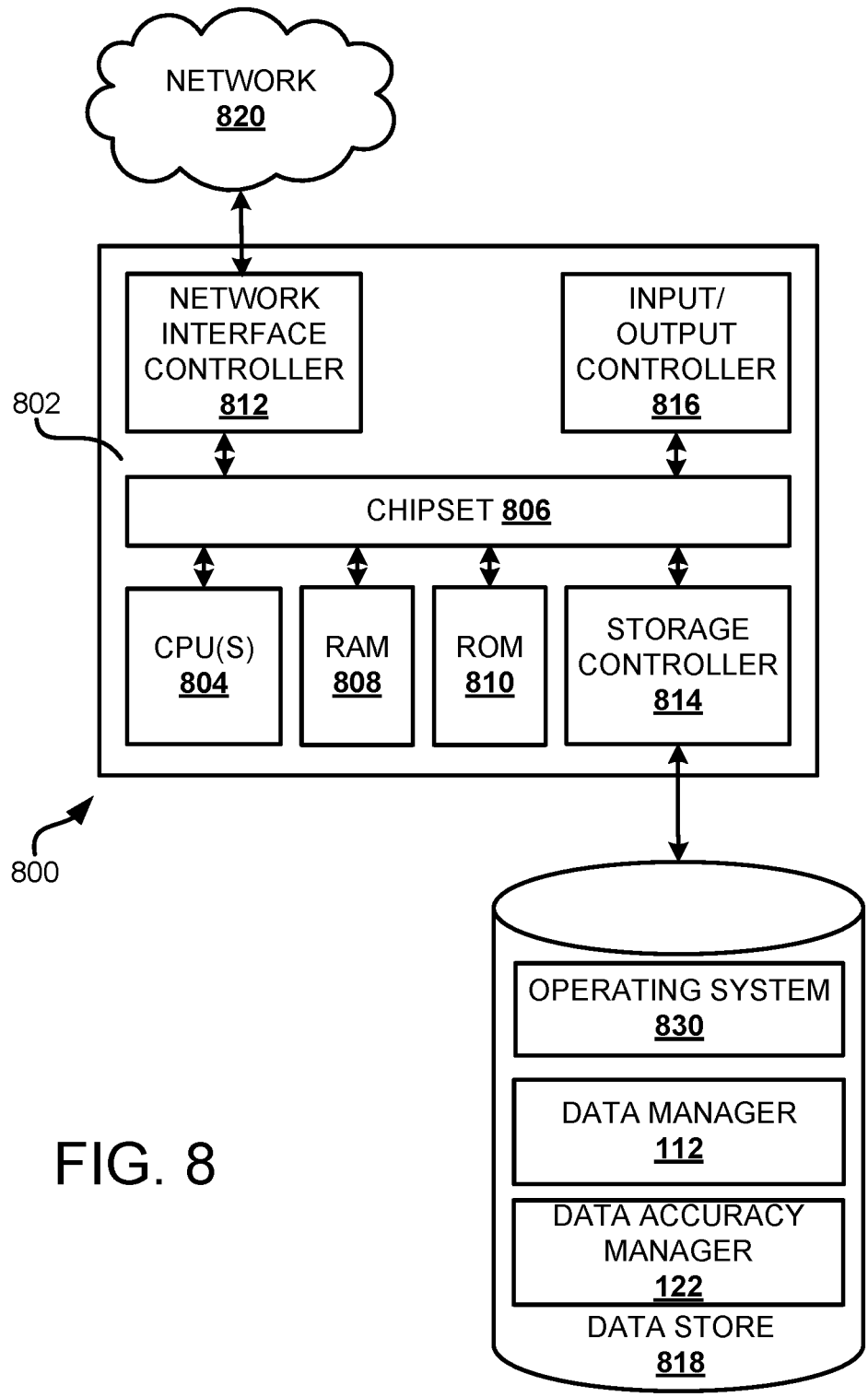
FIG. 8 is a computer architecture diagram showing one illustrative computer hardware architecture for implementing a computing device that might be utilized to implement aspects of the various examples presented herein.

FIG. 8 shows an example computer architecture for a computer 800 capable of executing program components for improving the accuracy of test data outside of a clinical setting in the manner described above. The computer architecture shown in FIG. 8 illustrates a conventional server computer, workstation, desktop computer, laptop, tablet, network appliance, digital cellular phone, smart watch, or other computing device, and may be utilized to execute any of the software components presented herein. For example, the computer architecture shown in FIG. 8 may be utilized to execute software components for performing operations as described above. The computer architecture shown in FIG. 8 might also be utilized to implement a computing device 102, or any other of the computing systems described herein.

The computer 800 includes a baseboard 802, or "motherboard," which is a printed circuit board to which a multitude of components or devices may be connected by way of a system bus or other electrical communication paths. In one illustrative example, one or more central processing units ("CPUs") 804 operate in conjunction with a chipset 806. The CPUs 804 may be standard programmable processors that perform arithmetic and logical operations necessary for the operation of the computer 800.

The CPUs 804 perform operations by transitioning from one discrete, physical state to the next through the manipulation of switching elements that differentiate between and change these states. Switching elements may generally include electronic circuits that maintain one of two binary states, such as flip-flops and electronic circuits that provide an output state based on the logical combination of the states of one or more other switching elements, such as logic gates. These basic switching elements may be combined to create more complex logic circuits, including registers, adders-subtractors, arithmetic logic units, floating-point units and the like.

The chipset 806 provides an interface between the CPUs 804 and the remainder of the components and devices on the baseboard 802. The chipset 806 may provide an interface to a RAM 808, used as the main memory in the computer 800. The chipset 806 may further provide an interface to a computer-readable storage medium such as a read-only memory ("ROM") 810 or non-volatile RAM ("NVRAM") for storing basic routines that help to startup the computer 800 and to transfer information between the various components and devices. The ROM 810 or NVRAM may also store other software components necessary for the operation of the computer 800 in accordance with the examples described herein.

The computer 800 may operate in a networked environment using logical connections to remote computing devices and computer systems through a network, such as the network 820. The chipset 806 may include functionality for providing network connectivity through a network interface controller ("NIC") 812, such as a mobile cellular network adapter, WiFi network adapter or gigabit Ethernet adapter. The NIC 812 is capable of connecting the computer 800 to other computing devices over the network 820. It should be appreciated that multiple NICs 812 may be present in the computer 800, connecting the computer to other types of networks and remote computer systems.

The computer 800 may be connected to a mass storage device 818 that provides non-volatile storage for the computer. The mass storage device 818 may store system programs, application programs, other program modules and data, which have been described in greater detail herein. The mass storage device 818 may be connected to the computer 800 through a storage controller 814 connected to the chipset 806. The mass storage device 818 may consist of one or more physical storage units. The storage controller 814 may interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 800 may store data on the mass storage device 818 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 818 is characterized as primary or secondary storage and the like.

For example, the computer 800 may store information to the mass storage device 818 by issuing instructions through the storage controller 814 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 800 may further read information from the mass storage device 818 by detecting the physical states or characteristics of one or more particular locations within the physical storage units.

In addition to the mass storage device 818 described above, the computer 800 may have access to other computer-readable storage media to store and retrieve information, such as program modules, data structures, or other data. It should be appreciated by those skilled in the art that computer-readable storage media is any available media that provides for the non-transitory storage of data and that may be accessed by the computer 800.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 818 may store an operating system 830 utilized to control the operation of the computer 800. According to one example, the operating system comprises the LINUX operating system. According to another example, the operating system comprises the WINDOWS® SERVER operating system from MICROSOFT Corporation. According to another example, the operating system comprises the iOS operating system from Apple. According to another example, the operating system comprises the Android operating system from Google or its ecosystem partners. According to further examples, the operating system may comprise the UNIX operating system. It should be appreciated that other operating systems may also be utilized. The mass storage device 818 may store other system or application programs and data utilized by the computer 800, such as components that include the data manager 122, the data accuracy manager 132 and/or any of the other software components and data described above. The mass storage device 818 might also store other programs and data not specifically identified herein.

In one example, the mass storage device 818 or other computer-readable storage media is encoded with computer-executable instructions that, when loaded into the computer 800, create a special-purpose computer capable of implementing the examples described herein. These computer-executable instructions transform the computer 800 by specifying how the CPUs 804 transition between states, as described above. According to one example, the computer 800 has access to computer-readable storage media storing computer-executable instructions which, when executed by the computer 800, perform the various routines described above with regard to FIGS. 4-8. The computer 800 might also include computer-readable storage media for performing any of the other computer-implemented operations described herein.

The computer 800 may also include one or more input/output controllers 816 for receiving and processing input from a number of input devices, such as a keyboard, a mouse, a touchpad, a touch screen, an electronic stylus, or other type of input device. Similarly, the input/output controller 816 may provide output to a display, such as a computer monitor, a flat-panel display, a digital projector, a printer, a plotter, or other type of output device. It will be appreciated that the computer 800 may not include all of the components shown in FIG. 8, may include other components that are not explicitly shown in FIG. 8, or may utilize an architecture completely different than that shown in FIG. 8.

Based on the foregoing, it should be appreciated that technologies for improving the accuracy of the test data obtained outside a clinical setting have been presented herein. Moreover, although some of the subject matter presented herein has been described in language specific to computer structural features, methodological acts and computer readable media, it is to be understood that the invention defined in the appended claims is not necessarily limited to the specific features, acts, or media described herein. Rather, the specific features, acts and media are disclosed as example forms of implementing at least some of the claims.

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the true spirit and scope of the present invention, which is set forth in the following claims.

What is claimed is:

1. A method, comprising:
   receiving test data associated with performance of one or more tests in a non-clinical setting, wherein the one or more tests are associated with an identification of one or more nutritional responses, the test data including at least food data, biome data, device test data captured by an electronic device, lab test data, and user generated data;
   utilizing a first machine learning mechanism to determine an accuracy of the test data;
   utilizing a second machine learning mechanism to determine adjusted test data;
   determining a quality score utilizing the first machine learning mechanism and wherein generating the quality score comprises:
   generating a food data score that provides an indication of a quality of the food data received;
   generating a biome data score that provides an indication of a quality of the biome data;
   generating a device test data score that provides an indication of a quality of the device test data;
   generating a lab test data score that provides an indication of a quality of the lab test data; and
   generating a user test data score that provides an indication of a quality of the user generated data; and
   adjusting, based at least in part on the accuracy of the test data and the quality score, a third machine learning mechanism which uses the adjusted test data as an input, wherein adjusting the third machine learning mechanism further comprises adjusting a weighting associated with the third machine learning mechanism based at least in part on the accuracy of the test data.

2. The method of claim 1, wherein the food data indicates one or more foods consumed by the individual to evoke a nutritional response.

3. The method of claim 1, wherein determining the accuracy of the test data comprises identifying one or more of a food classification error, a food quantity estimation error, or a food timing error.

4. The method of claim 1, wherein determining the accuracy of the test data comprises generating a score for the test data, wherein the score provides an indication of the accuracy of the test data, and wherein generating the score includes applying a fourth machine learning mechanism to the test data to generate test accuracy data.

5. The method of claim 1, further comprising generating a graphical user interface that includes user interface elements associated with the test data, causing the graphical user interface to be presented on a display, and receiving adjusted data in response to an interaction with one or more of the user interface elements.

6. The method of claim 1, further comprising generating one or more of a recommendation or a prediction using at least a portion of the test data that has been adjusted.

7. The method of claim 1, wherein causing, based at least in part on the accuracy of the test data, performance of actions comprising confirming the test data.

8. The method of claim 1, further comprising generating, based at least in part on the accuracy of the test data, a classification for the test data.

9. A system, comprising:
   a data ingestion service, including one or more processors, configured to:
   receive test data associated with performance of one or more tests in a non-clinical setting, wherein the one or more tests is associated with an identification of one or more nutritional responses;
   determine an accuracy of the test data utilizing a first machine learning mechanism;
   generate an indication of quality associated with the test data utilizing the first machine learning mechanism, wherein generating the indication of quality further comprises:
   generating a food data score that provides an indication of a quality of food data received;
   generating a biome data score that provides an indication of a quality of biome data associated with an individual associated with the test data;
   generating a device test data score that provides an indication of a quality of device test data captured by an electronic device, and
   generating a lab test data score that provides an indication of a quality of lab test data; and
   adjust, based at least in part on the accuracy of the test data and the indication of quality, a second machine learning mechanism which uses the test data as an input, wherein adjusting the second machine learning mechanism further comprises adjusting a weighting associated with the second machine learning mechanism based at least in part on the accuracy of the test data.

10. The system of claim 9, wherein the food data indicates one or more foods consumed by one or more individuals to evoke a nutritional response.

11. The system of claim 9, wherein determining the accuracy of the test data comprises generating a score for the test data, wherein the score provides an indication of the accuracy of the test data, and wherein generating the score comprises performing one or more of applying a machine learning mechanism to the test data to generate test accuracy data or receiving the test data from an input device associated with an authorized user.

12. The system of claim 9, wherein the data ingestion service is further configured to generate a user interface, cause the user interface to be presented, and receive adjusted data in response to an interaction with the user interface.

13. The system of claim 9, wherein the test data includes data from a plurality of individuals.

14. The system of claim 9, further comprising a service configured to generate one or more of a recommendation or a prediction using at least a portion of the test data that has been adjusted.

15. A non-transitory computer-readable storage medium having computer-executable instructions stored thereupon which, when executed by a computer, cause the computer to:
   receive test data associated with performance of one or more tests in a non-clinical setting, wherein the one or more tests is associated with an identification of one or more nutritional responses and the test data comprises one or more of:
   food data indicating one or more foods consumed by an individual to evoke a nutritional response,
   biome data associated with the individual,
   device test data captured by one or more electronic devices configured to measure one or more biological markers, or
   lab test data provided to one or more labs for analysis;
   determine an accuracy of the test data utilizing a first machine learning mechanism;
   generate one or more quality indications for the test data utilizing the first machine learning mechanism wherein generating the indication of quality further comprises:
   generating a food data score that provides an indication of a quality of food data received;
   generating a biome data score that provides an indication of a quality of biome data associated with an individual associated with the test data;
   generating a device test data score that provides an indication of a quality of device test data captured by an electronic device, and
   generating a lab test data score that provides an indication of a quality of lab test data; and
   cause, based at least in part on the accuracy of the test data and the one or more quality indications, an adjustment to a second machine learning mechanism which uses the test data as an input, wherein adjusting the second machine learning mechanism further comprises adjusting a weighting associated with the second learning mechanism based at least in part on the accuracy of the test data.

16. The non-transitory computer-readable storage medium of claim 15, wherein generating the one or more quality indications comprises one or more of: generating a food data score that provides an indication of a quality of food data received; generating a biome data score that provides an indication of a quality of biome data associated with the individual; generating a device test data score that provides an indication of a quality of device test data captured by an electronic device, or generating a lab test data score that provides an indication of a quality of lab test data.

17. The non-transitory computer-readable storage medium of claim 15, wherein determining the accuracy of the test data comprises receiving data from a user interface associated with one or more users.

18. The non-transitory computer-readable storage medium of claim 15, wherein causing, based at least in part on the accuracy of the test data, performance of actions comprising confirming the test data.

* * * * *